US009550784B2

(12) United States Patent
Leclercq et al.

(10) Patent No.: US 9,550,784 B2
(45) Date of Patent: Jan. 24, 2017

(54) INHIBITORS OF PHOSPHODIESTERASE 10 ENZYME

(71) Applicant: Janssen Pharmaceutica NV, Beerse (BE)

(72) Inventors: Laurent Christian L. Leclercq, Liège (BE); José Manuel Bartolomé-Nebreda, Toledo (ES); Susana Conde-Ceide, Toledo (ES); Michiel Luc Maria Van Gool, Madrid (ES)

(73) Assignee: Beerse Pharmaceutica NV, Beerse (BE)

( * ) Notice: Subject to any disclaimer, the term of this patent is extended or adjusted under 35 U.S.C. 154(b) by 0 days.

(21) Appl. No.: 14/413,775

(22) PCT Filed: Jul. 8, 2013

(86) PCT No.: PCT/EP2013/064355
§ 371 (c)(1),
(2) Date: Jan. 9, 2015

(87) PCT Pub. No.: WO2014/009305
PCT Pub. Date: Jan. 16, 2014

(65) Prior Publication Data
US 2015/0203498 A1    Jul. 23, 2015

(30) Foreign Application Priority Data
Jul. 9, 2012   (EP) .................................... 12175612

(51) Int. Cl.
C07D 487/04    (2006.01)

(52) U.S. Cl.
CPC .................................. C07D 487/04 (2013.01)

(58) Field of Classification Search
CPC .................................................. C07D 487/04
See application file for complete search history.

(56) References Cited

U.S. PATENT DOCUMENTS

| | | | |
|---|---|---|---|
| 4,242,513 A | 12/1980 | Hoover |
| 4,713,381 A | 12/1987 | Ao |
| 5,137,876 A | 8/1992 | MacCoss |
| 5,317,019 A | 5/1994 | Bender |
| 5,360,796 A | 11/1994 | Hansen, Jr. |
| 5,486,525 A | 1/1996 | Summers, Jr. |
| 5,498,774 A | 3/1996 | Mitsudera |
| 6,054,587 A | 4/2000 | Reddy |
| 6,245,769 B1 | 6/2001 | Arvanitis |
| 6,248,755 B1 | 6/2001 | Chapman |
| 6,352,990 B1 | 3/2002 | McCarthy |
| 6,403,588 B1 | 6/2002 | Hayakawa |
| 6,589,947 B1 | 7/2003 | Hamanaka |
| 6,777,395 B2 | 8/2004 | Bhat |
| 6,806,268 B2 | 10/2004 | Gall |
| 6,844,341 B2 | 1/2005 | Thomas |
| 6,855,719 B1 | 2/2005 | Thomas |
| 6,900,217 B2 | 5/2005 | Chen |
| 6,936,617 B2 | 8/2005 | Hutchison |
| 6,992,080 B2 | 1/2006 | Dwyer |
| 6,992,188 B1 | 1/2006 | Chen |
| 7,074,801 B1 | 7/2006 | Yoshida |
| 7,078,405 B2 | 7/2006 | Hibi |
| 7,078,410 B2 | 7/2006 | Berg |
| 7,105,533 B2 | 9/2006 | Campbell |
| 7,132,426 B2 | 11/2006 | Jones |
| 7,148,353 B2 | 12/2006 | Fang |
| 7,186,714 B2 | 3/2007 | Gudmundsson |
| 7,186,740 B2 | 3/2007 | Paruch |
| 7,186,832 B2 | 3/2007 | Sun |
| 7,189,723 B2 | 3/2007 | Mitchell |
| 7,196,095 B2 | 3/2007 | Biftu |
| 7,244,740 B2 | 7/2007 | Gudmundsson |
| 7,259,164 B2 | 8/2007 | Mitchell |
| 7,306,631 B2 | 12/2007 | Glenn, Jr. |
| 7,312,341 B2 | 12/2007 | DeSimone |
| 7,320,995 B2 | 1/2008 | Bonjouklian |
| 7,348,359 B2 | 3/2008 | Gardinier |
| 7,393,848 B2 | 7/2008 | Currie |
| 7,405,295 B2 | 7/2008 | Currie |
| 7,417,041 B2 | 8/2008 | Blumberg |
| 7,491,716 B2 | 2/2009 | Engler |
| 7,504,404 B2 | 3/2009 | McArthur |

(Continued)

FOREIGN PATENT DOCUMENTS

| | | |
|---|---|---|
| CA | 2398956 A1 | 8/2001 |
| CA | 2668738 A1 | 7/2008 |

(Continued)

OTHER PUBLICATIONS

International Search Report for PCT/EP2013/064355 dated Oct. 10, 2013.
International Search Report for PCT/EP2011/053445 dated Aug. 18, 2011.
International Search Report for PCT/EP2010/066264 dated Aug. 12, 2010.
Belanger, et al. "Discovery of imidazo[1,2-a]pyrazine-based Aurora kinase inhibitors", Bioorganic & Medicinal Chemistry Letters (2010), 20(17), 5170-5174.
Belanger, et al. "Discovery of orally bioavailable imidazo[1,2-a]pyrazine-based Aurora kinase inhibitors", Bioorganic & Medicinal Chemistry Letters (2010), 20(22), 6739-6743.
Bertelsen, et al., Arch Gen Psychiatry, 65:762 (2008).
Bouloc, et al. "Structure-based design of imidazo[1,2-a]pyrazine derivatives as selective inhibitors of Aurora-A kinase in cells", Bioorganic & Medicinal Chemistry Letters (2010), 20(20), 5988-5993.

(Continued)

Primary Examiner — Rebecca Anderson

(57) ABSTRACT

The present invention relates to novel imidazo[1,2-b]pyridazine and imidazo[1,2-a]-pyrazine derivatives which are inhibitors of the phosphodiesterase 10 enzyme (PDE10) and which may be useful for the treatment or prevention of neurological, psychiatric and metabolic disorders in which the PDE10 enzyme is involved. The invention is also directed to pharmaceutical compositions comprising such compounds, to processes to prepare such compounds and compositions, to the use of such compounds or pharmaceutical compositions for the prevention or treatment of neurological, psychiatric and metabolic disorders and diseases.

13 Claims, No Drawings

(56) References Cited

U.S. PATENT DOCUMENTS

| | | |
|---|---|---|
| 7,511,040 B2 | 3/2009 | Belanger |
| 7,557,103 B2 | 7/2009 | Collins |
| 7,563,797 B2 | 7/2009 | Araldi |
| 7,572,807 B2 | 8/2009 | Li |
| 7,576,085 B2 | 8/2009 | Guzi |
| 7,622,584 B2 | 11/2009 | Kim |
| 7,666,880 B2 | 2/2010 | Lee |
| 7,674,801 B2 | 3/2010 | Basarab |
| 8,716,282 B2 | 5/2014 | Pastor-Fernandez et al. |
| 2001/0041673 A1 | 11/2001 | Fossa |
| 2002/0049208 A1 | 4/2002 | Bakthavatchalam |
| 2003/0027820 A1 | 2/2003 | Gall |
| 2004/0014957 A1 | 1/2004 | Eldrup |
| 2004/0058938 A1 | 3/2004 | Cullmann |
| 2005/0031588 A1 | 2/2005 | Sommadossi |
| 2005/0079176 A1 | 4/2005 | Pierson, III |
| 2005/0079387 A1 | 4/2005 | Lee |
| 2005/0165232 A1 | 7/2005 | Beresis |
| 2005/0234029 A1 | 10/2005 | Dodic |
| 2005/0245520 A1 | 11/2005 | Dodic |
| 2005/0288295 A1 | 12/2005 | Currie |
| 2006/0094699 A1 | 5/2006 | Kampen |
| 2006/0100235 A1 | 5/2006 | Andersen |
| 2006/0135517 A1 | 6/2006 | Lee |
| 2006/0154105 A1 | 7/2006 | Yamamoto |
| 2006/0178367 A1 | 8/2006 | Currie |
| 2006/0258722 A1 | 11/2006 | Yasuma |
| 2007/0004736 A1 | 1/2007 | Kubo |
| 2007/0049591 A1 | 3/2007 | Pinkerton |
| 2007/0078136 A1 | 4/2007 | Vaccaro |
| 2007/0099925 A1 | 5/2007 | Calderwood |
| 2007/0105864 A1 | 5/2007 | Guzi |
| 2007/0117804 A1 | 5/2007 | Zhao |
| 2007/0149535 A1 | 6/2007 | Berset |
| 2007/0185063 A1 | 8/2007 | Storer |
| 2007/0197507 A1 | 8/2007 | Morgan |
| 2007/0219205 A1 | 9/2007 | Brenchley |
| 2008/0021217 A1 | 1/2008 | Borchardt |
| 2008/0045536 A1 | 2/2008 | Vaccaro |
| 2008/0070894 A1 | 3/2008 | Kawamura |
| 2008/0102028 A1 | 5/2008 | Morel |
| 2008/0103136 A1 | 5/2008 | Sato |
| 2008/0113978 A1 | 5/2008 | Barbosa |
| 2008/0161341 A1 | 7/2008 | Calderwood |
| 2008/0167314 A1 | 7/2008 | Uchikawa |
| 2008/0207634 A1 | 8/2008 | Gudmundsson |
| 2008/0221092 A1 | 9/2008 | Bluhm |
| 2008/0242862 A1 | 10/2008 | Calderwood |
| 2008/0255358 A1 | 10/2008 | Bamford |
| 2008/0300242 A1 | 12/2008 | Kuntz |
| 2008/0305081 A1 | 12/2008 | Hashihayata |
| 2008/0318975 A1 | 12/2008 | Wagner |
| 2009/0005374 A1 | 1/2009 | Melvin, Jr. |
| 2009/0023737 A1 | 1/2009 | Xu |
| 2009/0054409 A1 | 2/2009 | Andrews |
| 2009/0124625 A1 | 5/2009 | Bessis |
| 2009/0143376 A1 | 6/2009 | Milburn |
| 2009/0153035 A1 | 6/2009 | Shin |
| 2009/0156604 A1 | 6/2009 | Holder |
| 2009/0175852 A1 | 7/2009 | Ciavarri |
| 2009/0176778 A1 | 7/2009 | Schmitz |
| 2009/0203732 A1 | 8/2009 | Dhanak |
| 2009/0209573 A1 | 8/2009 | Wu |
| 2009/0215818 A1 | 8/2009 | Adams |
| 2009/0270436 A1 | 10/2009 | Iino |
| 2009/0317361 A1 | 12/2009 | Cho |
| 2009/0325953 A1 | 12/2009 | Sahoo |
| 2010/0029633 A1 | 2/2010 | Allen |
| 2010/0029638 A1 | 2/2010 | Melvin, Jr. |
| 2010/0063068 A1 | 3/2010 | Pracitto |

FOREIGN PATENT DOCUMENTS

| | | |
|---|---|---|
| CL | 3212-2007 | 6/2008 |
| EP | 0728759 | 8/1996 |
| EP | 1 293 213 A1 | 3/2003 |
| IT | 1374954 B1 | 5/2010 |
| JP | 6247969 A | 9/1994 |
| JP | 2001-006877 | 1/2001 |
| JP | 2001-057292 A | 2/2001 |
| JP | 2003-313126 A | 11/2003 |
| JP | 2004-002826 A | 1/2004 |
| JP | 2005-343889 A | 12/2005 |
| WO | WO 90/15534 A1 | 12/1990 |
| WO | WO 91/19497 A1 | 12/1991 |
| WO | WO 92/10190 A1 | 6/1992 |
| WO | WO 92/10498 A1 | 6/1992 |
| WO | WO 96/34866 A1 | 11/1996 |
| WO | WO 02/34748 A1 | 5/2002 |
| WO | WO 02/066478 A1 | 8/2002 |
| WO | WO 2004/017950 A2 | 3/2004 |
| WO | WO 2004/026877 A1 | 4/2004 |
| WO | WO 2004/035579 A1 | 4/2004 |
| WO | WO 2004/075846 | 9/2004 |
| WO | WO 2004/087710 | 10/2004 |
| WO | WO 2004/089416 A2 | 10/2004 |
| WO | WO 2004/103991 A1 | 12/2004 |
| WO | WO 2005/014599 A1 | 2/2005 |
| WO | WO 2005/020885 A2 | 3/2005 |
| WO | WO 2005/047290 A2 | 5/2005 |
| WO | WO 2006/044509 A2 | 4/2006 |
| WO | WO 2006/102194 | 9/2006 |
| WO | WO 2007/003386 A1 | 1/2007 |
| WO | WO 2007/013673 A1 | 2/2007 |
| WO | WO 2007/048779 | 5/2007 |
| WO | WO 2007/087548 A2 | 8/2007 |
| WO | WO 2007/145921 A1 | 12/2007 |
| WO | WO 2008/003511 A1 | 1/2008 |
| WO | WO 2008/030579 A2 | 3/2008 |
| WO | WO 2008/030795 A2 | 3/2008 |
| WO | WO 2008/057402 A2 | 5/2008 |
| WO | WO 2008/079460 A2 | 7/2008 |
| WO | WO 2008/081910 A1 | 7/2008 |
| WO | WO 2008/121687 A2 | 10/2008 |
| WO | WO 2008/124153 A1 | 10/2008 |
| WO | WO 2008/133192 A1 | 11/2008 |
| WO | WO 2008/134553 A1 | 11/2008 |
| WO | WO 2008/138834 A1 | 11/2008 |
| WO | WO 2008/141079 A1 | 11/2008 |
| WO | WO 2008/156614 A2 | 12/2008 |
| WO | WO 2009/005675 A1 | 1/2009 |
| WO | WO 2009/016286 A2 | 2/2009 |
| WO | WO 2009/016560 A2 | 2/2009 |
| WO | WO 2009/017701 A2 | 2/2009 |
| WO | WO 2009/021990 A1 | 2/2009 |
| WO | WO 2009/023253 A2 | 2/2009 |
| WO | WO 2009/024585 A2 | 2/2009 |
| WO | WO 2009/037394 A2 | 3/2009 |
| WO | WO 2009/060197 A1 | 5/2009 |
| WO | WO 2009/061856 A1 | 5/2009 |
| WO | WO 2009/077334 | 6/2009 |
| WO | WO 2009/081857 A1 | 7/2009 |
| WO | WO 2009/086123 A1 | 7/2009 |
| WO | WO 2009/086130 A1 | 7/2009 |
| WO | WO 2009/097233 A1 | 8/2009 |
| WO | WO 2009/108546 A1 | 9/2009 |
| WO | WO 2009/112679 A1 | 9/2009 |
| WO | WO 2009/117157 A1 | 9/2009 |
| WO | WO 2009/124653 A2 | 10/2009 |
| WO | WO 2009/126691 A1 | 10/2009 |
| WO | WO 2009/143156 A2 | 11/2009 |
| WO | WO 2009/146358 | 12/2009 |
| WO | WO 2009/152072 A1 | 12/2009 |
| WO | WO 2010/002985 A1 | 1/2010 |
| WO | WO 2010/009155 A2 | 1/2010 |
| WO | WO 2010/011837 A1 | 1/2010 |
| WO | WO 2010/016005 A1 | 2/2010 |
| WO | WO 2010/018327 A1 | 2/2010 |
| WO | WO 2010/033906 A2 | 3/2010 |
| WO | WO 2010/036407 A2 | 4/2010 |
| WO | WO 2010/047279 A1 | 4/2010 |
| WO | WO 2010/048149 A2 | 4/2010 |
| WO | WO 2010/059836 A1 | 5/2010 |
| WO | WO 2010/059838 A2 | 5/2010 |

(56) References Cited

FOREIGN PATENT DOCUMENTS

| | | |
|---|---|---|
| WO | WO 2010/069684 A1 | 6/2010 |
| WO | WO 2010/084425 A1 | 7/2010 |
| WO | WO 2010/084690 A1 | 7/2010 |
| WO | WO 2010/088368 A2 | 8/2010 |
| WO | WO 2010/088518 A2 | 8/2010 |
| WO | WO 2010/098458 A1 | 9/2010 |
| WO | WO 2010/108074 A2 | 9/2010 |
| WO | WO 2010/110277 A1 | 9/2010 |
| WO | WO 2010/119264 A1 | 10/2010 |
| WO | WO 2011/013729 A1 | 2/2011 |
| WO | WO 2011/021520 A1 | 2/2011 |
| WO | WO 2011/051342 | 5/2011 |
| WO | WO 2011/059099 A1 | 5/2011 |
| WO | WO 2011/089400 A1 | 7/2011 |
| WO | WO 2011/110545 A1 | 9/2011 |
| WO | WO 2012/146644 A1 | 11/2012 |

OTHER PUBLICATIONS

Blokland et al., Expert Opin. Ther. Patents (2012) 22(4), pp. 349-354.
Carverley, M.J. Tetrahedron, 1987, 43(20), 4609-19.
Charych et al., The Journal of Neuroscience, Jul. 7, 2010 • 30(27):9027-9037.
Ennanceur, Behav Brain Res 1988, 31, 47-59.
Gaudry et al., Organic Syntheses, 1976, 55, 24-27.
Gehlert, et al. "3-(4-Chloro-2-morpholin-4-yl-thiazol-5-yl)-8-(1-ethylpropyl)-2,6-dimethyl-imidazo[1,2-b]pyridazine: a novel brain-penetrant, orally available corticotropin-releasing factor receptor 1 antagonist with efficacy in animal models of alcoholism", Journal of Neuroscience (2007), 27(10), 2718-2726.
Gennaro et al. Remington's Pharmaceutical Sciences (18$^{th}$ ed., Mack Publishing Company, 1990, see especially Part 8: Pharmaceutical preparations and their Manufacture), pp. 1435-1712 (split/uploaded into 4 separate files due to size).
Gudmundsson, et al. "Imidazo[1,2-a]pyridines with potent activity against herpesviruses", Bioorganic & Medicinal Chemistry Letters (2007), 17(10), 2735-2739.
Gudmundsson, et al. "Synthesis of Novel Imidazo[1,2-a]pyridines with Potent Activity against Herpesviruses", Organic Letters (2003), 5(8), 1369-1372 CODEN: ORLEF7; ISSN: 1523-7060.
Hebb et al., Current Opinion in Pharmacology 2007, 7:86-92.
Harig et al., J. Translational Med. 2:44 (2004).
Il'icheva, et al. "Theoretical Study of the Structure of Adenosine Deaminase Complexes with Adenosine Analogues: I. Aza-, Deaza-, and Isomeric Azadeazaanalogues of Adenosine", Russian Journal of Bioorganic Chemistry (2005), 31(5), 439-452.
Kehler et al., Expert Opin. Ther. Patents (2007) 17(2), pp. 147-158.
Kehler et al. Expert Opin. Ther. Patents (2009) 19(12), pp. 1715-1725.
Kehler, et al., Expert Opin. Ther. Pat., "Phosphodiesterase 10A inhibitors: a 2009-20012 patent update", pp. 1-15 (Dec. 5, 2012).
Kerekes, et al. "Aurora Kinase Inhibitors Based on the Imidazo[1,2-a]pyrazine Core: Fluorine and Deuterium Incorporation Improve Oral Absorption and Exposure" Journal of Medicinal Chemistry (2011), 54(1), 201-210.
Kobe, et al. "Use of distance geometry approach for the in vitro antiviral activity evaluation of N-bridgehead C-nucleosides", European Journal of Medicinal Chemistry (1992), 27(3), 259-66.
Kolar, et al. "Transformations of the pyrido[1,2-a]pyrazine ring system into imidazo[1,2-a]pyridines, imidazo[1,2-a]pyrimidines and 2-oxa-6a,10c-diazaaceanthrylenes", Journal of Heterocyclic Chemistry (1996), 33(3), 639-642.
Lhassani, et al. "Synthesis and antiviral activity of imidazo[1,2-a]pyridines", European Journal of Medicinal Chemistry (1999), 34(3), 271-274.
MacCoss, et al. "Synthesis and biological evaluation of nucleosides containing 8-aminoimidazo[1,2-a]pyrazine as an isosteric replacement for adenine", Journal of Heterocyclic Chemistry (1993), 30(5), 1213-20.
Meng, et al. "Bioisosteric approach to the discovery of imidazo[1,2-a]pyrazines as potent Aurora kinase inhibitors" Bioorganic & Medicinal Chemistry Letters (2011), 21(1), 592-598.
Pan, et al. "Synthesis of novel isoxazolinyl substituted imidazo[1,2-a]pyridine C-nucleoside analogs", Tetrahedron Letters (1998), 39(45), 8191-8194.
Siuciak, Judith A., CNS Drugs 2008; 22 (12): 983-993.
Siuciak, et al., Expert Opin. Drug Discov. 2:1001 (2007).
van den Heuvel, M. et al.; J. Org. Chem., 2004, 250.
Wang, et al. "Synthesis of novel isoxazolinyl substituted imidazo]1,2-a]pyridine C-nucleoside analogs", Hecheng Huaxue (2001), 9(5), 386-389.
Wang, X. et al. Tetrahedron Lett., 2000, 4335-4338.
Yu, Tao et al. "Discovery of a Potent, Injectable Inhibitor of Aurora Kinases Based on the Imidazo-[1,2-a]-Pyrazine Core", ACS Medicinal Chemistry Letters (2010), 1(5), 214-218.
Zarubin, et al. "Theoretical study of adenosine and its isosteric analogs. A possible mechanism of their binding in an active site of mammalian adenosine deaminase", Vestnik Samarskogo Gosudarstvennogo Universiteta, Estestvennonauchnaya Seriya (2003), (Spec.), 152-173.
Owen, et al, "Structure-activity relationships of novel non-competitive mGluR1 antagonists: A potential treatment for chronic pain", Bioorganic & Medicinal Chemistry, Letters, (2007), vol. 17, No. 2, pp. 486-490.
Schmidt et al., "Preclinical Characterization of Selective Phosphodiesterase 10A Inhibitors: A New therapeutic Approach to the Treatment of Schizophrenia", The Journal of Pharmacology and Experimental Therapeutics, (2008), vol. 325, No. 2, pp. 681-690.

INHIBITORS OF PHOSPHODIESTERASE 10 ENZYME

CROSS REFERENCE TO RELATED APPLICATIONS

This application is the national stage of PCT Application No. PCT/EP2013/064355, filed Jul. 8, 2013, the entire disclosure of which is hereby incorporated in its entirety, which claims priority from European Patent Application No. 12175612.6, flied Jul. 9, 2012.

FIELD OF THE INVENTION

The present invention relates to novel imidazo[1,2-b]pyridazine and imidazo[1,2-a]-pyrazine derivatives which are inhibitors of the phosphodiesterase 10 enzyme (PDE10) and which may be useful for the treatment or prevention of neurological, psychiatric and metabolic disorders in which the PDE10 enzyme is involved. The invention is also directed to pharmaceutical compositions comprising such compounds, to processes to prepare such compounds and compositions, to the use of such compounds or pharmaceutical compositions for the prevention or treatment of neurological, psychiatric and metabolic disorders and diseases.

BACKGROUND ART

Phosphodiesterases (PDEs) are a family of enzymes encoded by 21 genes and subdivided into 11 distinct families according to structural and functional properties. These enzymes metabolically inactivate widely occurring intracellular second messengers, 3',5'-cyclic adenosine monophosphate (cAMP) and 3',5'-cyclic guanosine monophosphate (cGMP). These two messengers regulate a wide variety of biological processes, including pro-inflammatory mediator production and action, ion channel function, muscle contraction, learning, differentiation, apoptosis, lipogenesis, glycogenolysis, and gluconeogenesis. They do this by activation of protein kinase A (PKA) and protein kinase G (PKG), which in turn phosphorylate a wide variety of substrates including transcription factors and ion channels that regulate innumerable physiological responses. In neurons, this includes the activation of cAMP and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by PDEs. PDEs are hydrolases that inactivate cAMP and cGMP by catalytic hydrolysis of the 3'-ester bond, forming the inactive 5'-monophosphate (Scheme A).

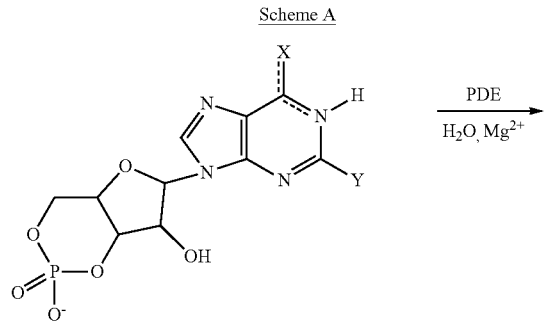

Scheme A cAMP X = NH$_2$, Y = H
cGMP X = O, Y = NH$_2$

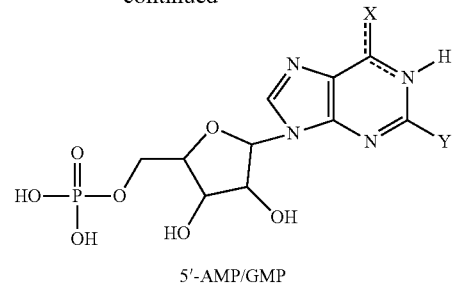

5'-AMP/GMP

On the basis of substrate specificity, the PDE families can be divided into three groups: i) the cAMP-specific PDEs, which include PDE4, 7 and 8; ii) the cGMP-selective enzymes PDES, 6, and 9; and iii) the dual-substrate PDEs, PDE1, 2 and 3, as well as PDE10 and 11.

Furthermore, PDEs are expressed differentially throughout the organism, including the central nervous system. Different PDE isozymes therefore may have different physiological functions. Compounds that inhibit selectively PDE families or isozymes may display particular therapeutic activity, fewer side effects, or both.

The discovery of phosphodiesterase 10A (PDE10A) was reported in 1999. Of all the 11 known PDE families, PDE10 has the most restricted distribution with high expression only in the brain and testes.

In the brain, PDE10A mRNA and protein are highly expressed in a majority of striatal Medium Spiny Neurons (MSNs). This unique distribution of PDE10A in the brain, together with its increased pharmacological characterization, indicates a potential use of PDE10A inhibitors for treating neurological and psychiatric disorders like schizophrenia.

In the basal ganglia, MSNs constitute the major site for reception and integration of cortical glutamatergic and midbrain dopaminergic input, and form key output pathways that help discriminate and act on relevant and irrelevant cognitive and motor patterns. MSNs are GABAergic projection neurons evenly distributed between two distinct pathways. Striatonigral MSNs (in the direct pathway) express the D$_1$ dopamine receptor and neuropeptides dynorphin and substance P; striatopallidal MSNs (in the indirect pathway) express the D$_2$ dopamine receptors and neuropeptide enkephalin. D$_1$ dopamine receptors are positively coupled to cAMP production, while D$_2$ dopamine receptors are negatively coupled to cAMP production. These pathways affect the concentration of extracellular dopamine and modulate motor and behavioural responses.

PDE10 Inhibitors and Schizophrenia

Due to the predominant localisation of PDE10 in MSNs, the majority of research on PDE10 inhibitors has been focused on preclinical models of psychosis.

On the basis of studies performed on knockout mice, the effects of PDE10 inhibition on striatal gene expression have been compared to the effects induced by a D$_1$ agonist and a D$_2$ antagonist.

Schizophrenia is a severe and chronic mental illness that affects approximately 1% of the population. Clinical symptoms are apparent relatively early in life, generally emerging during adolescence or early adulthood. The symptoms of schizophrenia are usually divided into those described as positive, including hallucinations, delusions and disorganised thoughts and those referred to as negative, which include social withdrawal, diminished affection, poverty of speech and the inability to experience pleasure. In addition, schizophrenic patients suffer from cognitive deficits, such as impaired attention and memory. The aetiology of the disease is still unknown, but aberrant neurotransmitter actions have been hypothesized to underlie the symptoms of schizophrenia. The dopaminergic hypothesis is one most often considered, which proposes that hyperactivity of dopamine transmission is responsible for the positive symptoms observed in schizophrenic patients.

The efficacy of currently marketed antipsychotics correlates with their ability to block $D_2$ dopamine receptors. Acute and chronic administration of antipsychotics such as haloperidol has characteristic effects on striatal gene expression. Inhibition of PDE10A has also been observed to produce alterations in striatal gene expression similar to those exerted by haloperidol.

Atypical antipsychotics, such as clozapine, olanzapine, risperidone and paliperidone display a more beneficial profile of extrapyramidal side effects (EPS) and tardive dyskinesia associated with acute and long-term $D_2$ receptor blockade. However, there is still a need to develop novel antipsychotics with an extended therapeutic profile and less side effects, e.g. by using approaches beyond dopamine $D_2$ receptor blockade. Thus, PDE10 inhibitors may possess a pharmacological profile similar to that of the current antipsychotics which mainly treat positive symptoms of schizophrenia, but also having the potential to improve the negative and cognitive symptoms of schizophrenia, while lacking the non-target related side effects such as EPS or prolactin release, that are often observed with the currently available antipsychotics.

Since PDE10 inhibitors can be used to raise levels of cAMP and /or cGMP within cells that express the PDE10 enzyme, for example neurons that comprise the basal ganglia, PDE10 inhibitors may be useful in treating schizophrenia and additionally, a variety of conditions as described herein such as Parkinson's disease, Huntington's disease, addiction, and depression. PDE10 inhibitors may be also useful in other conditions such as obesity, non-insulin dependent diabetes, bipolar disorder, obsessive compulsive disorder and pain.

The efficacy of PDE10A inhibition in models of cognition and against negative symptoms of schizophrenia has also been suggested by recently reported in vivo studies in which this mechanism has been associated with increased sociality in the Social Approach/Social Avoidance assay, reversed effect of chronic MK-801 treatment in a forced swim test, enhancement of social odor recognition in mice and improved novel object recognition in rats.

BACKGROUND ART

WO 2011/051342, published on 5 May 2011, discloses imidazo[1,2-b]pyridazine compounds and their activity as inhibitors of phosphodiesterase 10 enzyme.

WO 2011/110545, published on 15 Sep. 2011, discloses imidazo[1,2-a]pyrazine derivatives and their activity as inhibitors of phosphodiesterase 10 enzyme.

DESCRIPTION OF THE INVENTION

It is the object of the present invention to provide novel hydroxyl-substituted compounds that are PDE10 inhibitors.

Thus, in one aspect, the present invention relates to a compound of Formula (I)

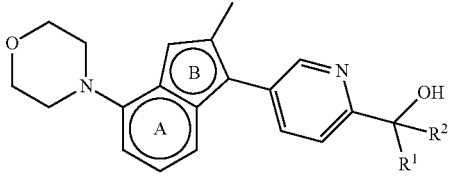

or a stereoisomeric form thereof, wherein
$R^1$ is H and $R^2$ is

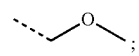

or wherein $R^1$ and $R^2$, taken together with the carbon atom to which they are attached, form a radical of Formula

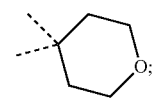

and
the bicycle

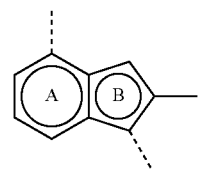

is a bicycle of Formula a)

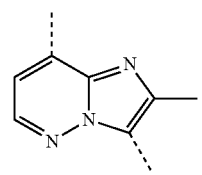

or of Formula b)

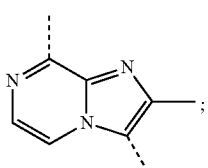

or a pharmaceutically acceptable salt or a solvate thereof.

The present invention also relates to a pharmaceutical composition comprising a therapeutically effective amount of a compound of Formula (I) or a stereoisomeric form thereof, or a pharmaceutically acceptable salt or a solvate thereof, and a pharmaceutically acceptable carrier or excipient.

Additionally, the invention relates to a compound of Formula (I) or a stereoisomeric form thereof, or a pharmaceutically acceptable salt or a solvate thereof, for use as a medicament, and to a compound of Formula (I) or a stereoisomeric form thereof, or a pharmaceutically acceptable salt or a solvate thereof, for use in the treatment or in the prevention of neurological, psychiatric or metabolic disorders and diseases.

Additionally, the invention relates to the use of a compound of Formula (I) or a stereoisomeric form thereof, or a pharmaceutically acceptable salt or a solvate thereof, in combination with an additional pharmaceutical agent for use in the treatment or prevention of neurological, psychiatric or metabolic disorders and diseases.

Furthermore, the invention relates to a process for preparing a pharmaceutical composition according to the invention, characterized in that a pharmaceutically acceptable carrier is intimately mixed with a therapeutically effective amount of a compound of Formula (I) or a stereoisomeric form thereof, or a pharmaceutically acceptable salt or a solvate thereof.

The invention also relates to a product comprising a compound of Formula (I) or a stereoisomeric form thereof, or a pharmaceutically acceptable salt or a solvate thereof, and an additional pharmaceutical agent, as a combined preparation for simultaneous, separate or sequential use in the treatment or prevention of neurological, psychiatric or metabolic disorders and diseases.

DETAILED DESCRIPTION OF THE INVENTION

The chemical names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006).

Definitions

The term "$C_{1-4}$alkyl" as used herein alone or as part of another group, defines a saturated, straight or branched, hydrocarbon radical having, unless otherwise stated, from 1 to 4 carbon atoms, such as methyl, ethyl, 1-propyl, 1-methylethyl, butyl, 1-methyl-propyl, 2-methyl-1-propyl,1,1-dimethylethyl and the like.

The term "halogen" or "halo" as used herein alone or as part of another group, refers to fluoro, chloro, bromo or iodo, with fluoro or chloro being preferred.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation or reversal of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "treatment" is intended to refer to all processes, wherein there may be a slowing, interrupting, arresting or stopping of the progression of a disease, but does not necessarily indicate a total elimination of all symptoms.

The term "compounds of the invention" defines compounds of Formula (I), stereoisomeric forms and salts and solvates thereof.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Conversely, said salt forms can be converted into the free base form by treatment with an appropriate base.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid.

Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethyl-amino)-ethanol, ethanolamine, ethylene-diamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Conversely, said salt forms can be converted into the free acid forms by treatment with an appropriate acid.

The term solvate comprises the solvent addition forms as well as the salts thereof, which the compounds of Formula (I) are able to form. Examples of such solvent addition forms are e.g. hydrates, alcoholates and the like.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

A compound of Formula (I) as defined herein, wherein R$^1$ is H and R$^2$ is

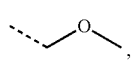

herein referred to as compound of Formula (I'), has one asymmetric carbon atom, as illustrated below, wherein the asymmetric carbon atom is identified by a *:

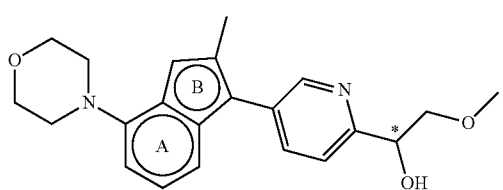

(I')

Thus, the compound of Formula (I) as defined herein, wherein R$^1$ is H and R$^2$ is

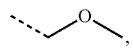

herein referred to as compound of Formula (I'), can form two different enantiomers, i.e. stereoisomers that are non-superimposable mirror images of each other, and can exist as either pure enantiomer or as mixtures thereof.

Accordingly, the definition of "compound of Formula (I)" includes the enantiomers of the compound of Formula (I) either as a pure enantiomer or as a mixture of the two enantiomers. A particular mixture according to the invention is a 1:1 mixture of the pair of enantiomers, also referred to as a racemate or a racemic mixture.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light. When a specific enantiomer is identified, this means that said enantiomer is substantially free, i.e. associated with less than 50%, preferably less than 20%, more preferably less than 10%, even more preferably less than 5%, in particular less than 2% and most preferably less than 1%, of the other enantiomer.

Thus, when a compound of Formula (I) is for instance specified as (R), this means that the compound is substantially free of the (S) enantiomer; when a compound of Formula (I) is for instance specified as (+), this means that the compound is substantially free of the (−) enantiomer.

The absolute stereochemical configuration of the compounds of Formula (I) and of the intermediates used in their preparation may be determined by those skilled in the art while using known methods such as, for example, X-ray diffraction.

As used herein, the notation "RS" denotes a racemic mixture, unless otherwise indicated; the notation "*R" or "*S" is used when the absolute stereochemistry is undetermined although the compound itself has been isolated as a single stereoisomer and is enantiomerically pure.

Thus, in a particular embodiment, the invention relates to a compound of Formula (I')

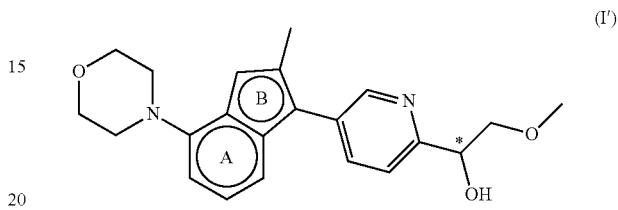

(I')

or a stereoisomeric form thereof, wherein the bicycle

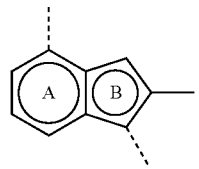

is a bicycle of Formula a)

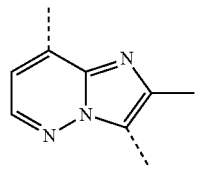

or of Formula b)

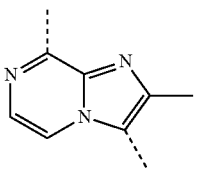

;

or a pharmaceutically acceptable salt or a solvate thereof

Thus, in a further particular embodiment, the invention relates to a compound of Formula (I') selected from compounds of Formula (I'-a) and (I'-b) as defined below:

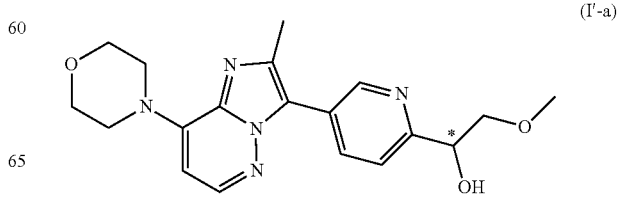

(I'-a)

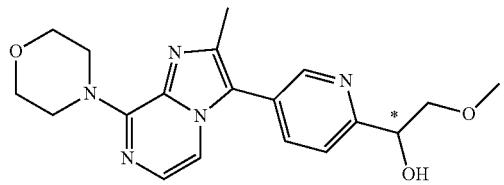
(I'-b)

or a stereoisomeric form thereof, or a pharmaceutically acceptable salt or a solvate thereof.

In a further embodiment, the invention relates to a compound of Formula (I'-a) in the form of substantially pure enantiomer (+)-(I'-a) ($[\alpha]^{20}_D$=+40.8° (c=0.5, DMF)) or in the form of substantially pure enantiomer (−)-(I'-a) ($[\alpha]^{20}_D$=−44.7° (c=0.5, DMF)), or a pharmaceutically acceptable salt or a solvate thereof An alternative notation for each of the enantiomers is

*R-(I'-a) or *S-(I'-a)

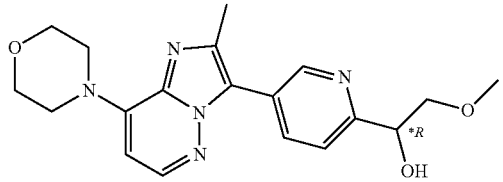
*R-(I'-a)

having an optical rotation [α]=−44.7° (589 nm, c 0.5 g/100 mL, DMF, 20° C.); or

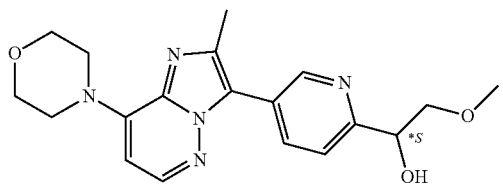
*S-(I'-a)

having an optical rotation [α]=+40.8° (589 nm, c 0.5 g/100 mL, DMF, 20° C.).

According to an additional embodiment, the invention relates to a compound of Formula (I) as defined herein, wherein $R^1$ and $R^2$ are taken together with the carbon atom to which they are attached to form a radical of Formula

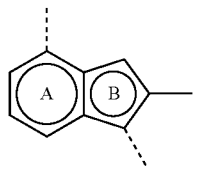
, herein referred to as compound of Formula (I″), represented below

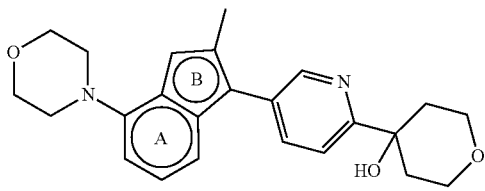
(I″)

wherein the bicycle

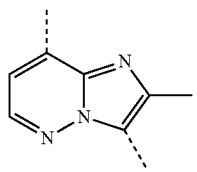

is a bicycle of Formula a)

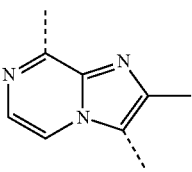

or of Formula b)

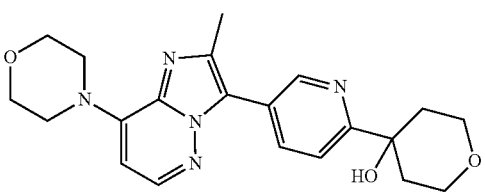

, or a pharmaceutically acceptable salt or a solvate thereof.

Thus, in a further particular embodiment, the invention relates to a compound of Formula (I″) selected from compounds of Formula (I″-a) and (I″-b) as defined below:

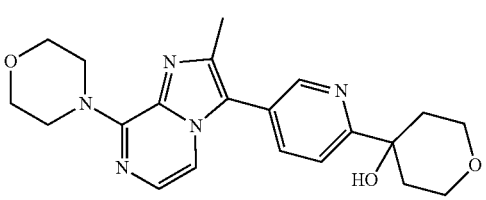
(I″-a)

(I″-b)

or a pharmaceutically acceptable salt or a solvate thereof.

PREPARATION

The compounds of the invention can generally be prepared by a succession of steps, each of which is known to the skilled person. In particular, the compounds can be prepared according to the following synthetic methods.

The compound of Formula (I), wherever appropriate, may be synthesized in the form of a racemic mixture of enantiomers which can be separated from one another following art-known resolution procedures. The racemic compounds of Formula (I) may be converted into the corresponding diastereomeric salt forms by reaction with a suitable chiral acid. Said diastereomeric salt forms may be subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

Experimental Procedure 1

The final compound according to Formula (I), can be prepared by a Suzuki coupling, by reacting an intermediate compound of Formula (II) wherein halo represents bromo or iodo with a boronic acid or a boronic ester of Formula (III), wherein $R^3$ and $R^4$ may each be independently selected from hydrogen or $C_{1-4}$alkyl, or may be taken together to form for example a bivalent radical of Formula —$CH_2$—$CH_2$—, —$CH_2$—$CH_2$—$CH_2$—, or —$C(CH_3)_2C(CH_3)_2$—, in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

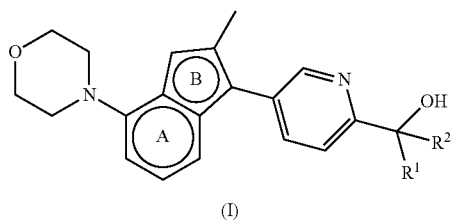

(I)

Experimental Procedure 1a

The final compound according to Formula (I), wherein the substituent —$CR^1R^2$(OH) is

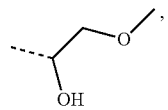

hereby referred to as compound of Formula (I'), can be prepared according to the general procedure described under Experimental procedure 1, wherein the compound of Formula (III) has the Formula (IIIa) wherein $R^3$ and $R^4$ are as defined for compound of Formula (III) above.

Reaction Scheme 1a

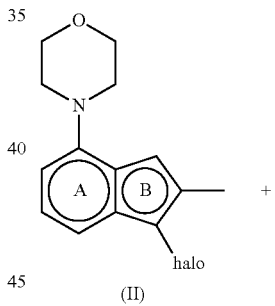

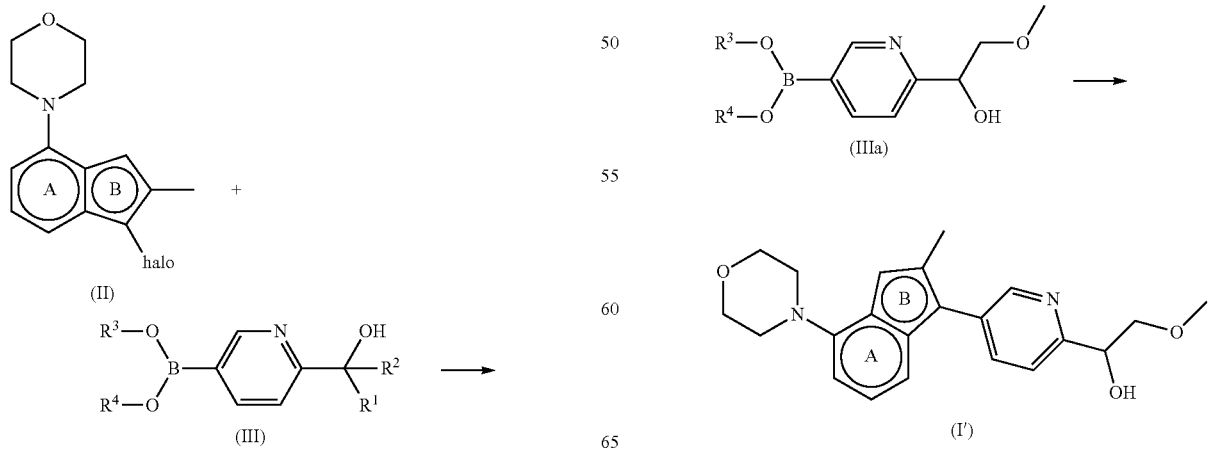

Experimental Procedure 1b

The final compound according to Formula (I), wherein the substituent —CR$^1$R$^2$(OH) is

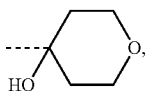

hereby referred to as compound of Formula (I″), can be prepared according to the general procedure described under Experimental procedure 1, wherein the compound of Formula (III) has the Formula (IIIb) wherein R$^3$ and R$^4$ are as defined for compound of Formula (III) above.

Reaction Scheme 1b

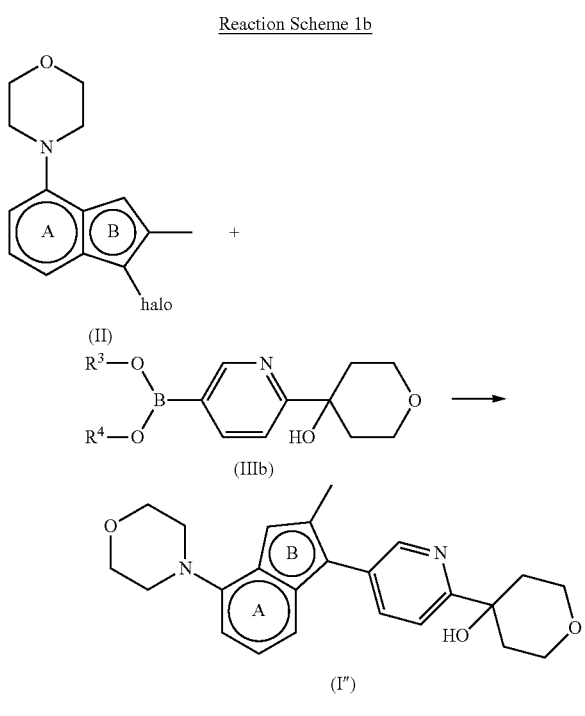

Experimental Procedure 2a

The intermediate compound according to Formula (II), wherein

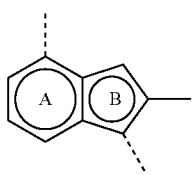

is a bicycle of Formula a)

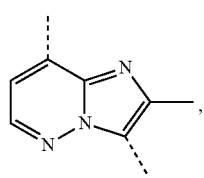

herein referred to as (IIa), can be prepared following the reaction steps described in WO 2011/051342, shown in the reaction scheme (2a) below Reaction Scheme 2a

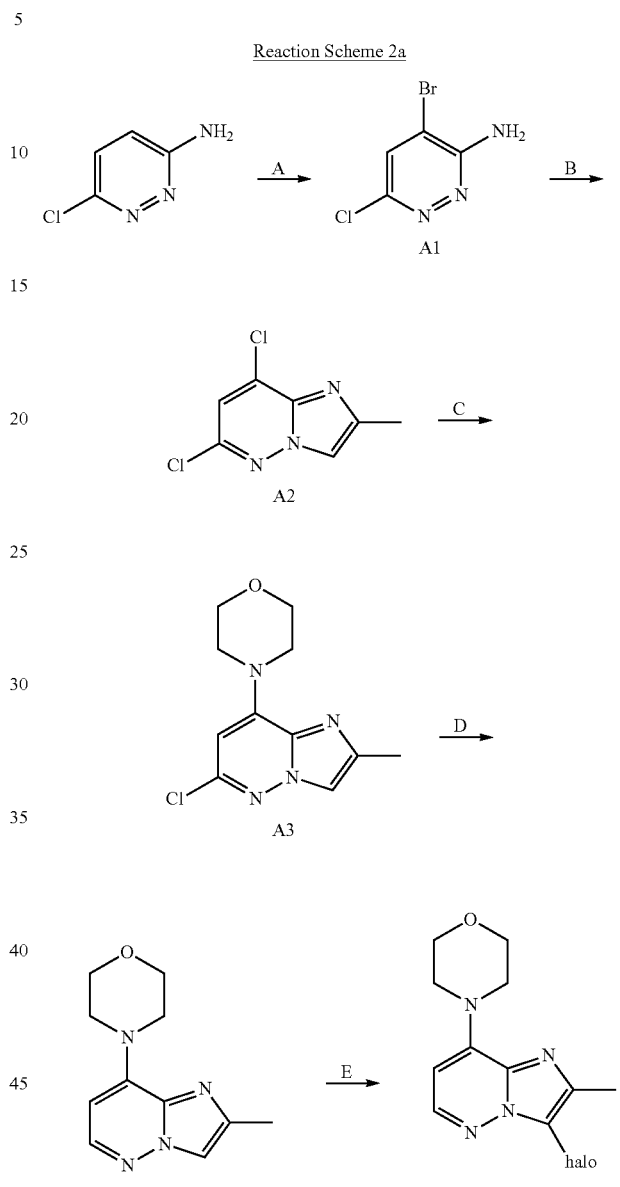

A: Bromination
B: Reaction with 2-chloropropanone
C: Reaction with morpholine
D: Dehalogenation
E: Halogenation Compounds of Formula (II) in the above reaction scheme (2a) can be prepared from commercially available materials via a five step (steps A-E) procedure.

In step E, a compound of Formula (IIa) can be prepared by reacting an intermediate of Formula A4 with N-bromo- or N-iodosuccinimide, in a suitable inert solvent, such as dichloromethane, in the presence of a suitable acid catalyst, such as acetic acid, under suitable reaction conditions, such as a convenient temperature, typically ranging between −10° C. and 40° C. A particular example of step E is described hereinbelow for the synthesis of intermediate A5.

Experimental Procedure 2b

The intermediate compound according to Formula (II), wherein

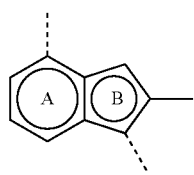

is a bicycle of Formula b)

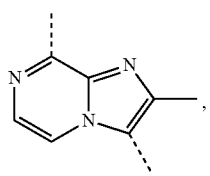

herein referred to as (IIb), can be prepared following the reaction steps described in WO 2011/110545, shown in the reaction scheme (2b) below Reaction Scheme 2b

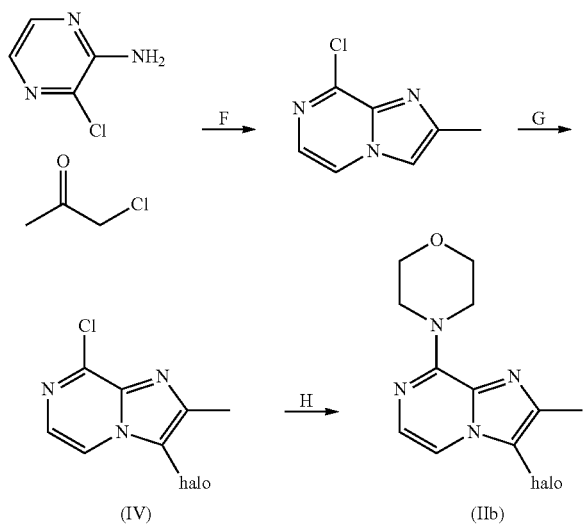

F: Reaction with 2-chloropropanone
G: Halogenation
H: Reaction with morpholine

Compounds of Formula (IIb) in the above reaction scheme (2b) can be prepared from commercially available materials via a three step (steps F-H) procedure.

Steps F-H can be performed under reaction conditions as detailed in WO 2011/051342. In step G, 8-chloro-2-methyl-imidazo[1,2-a]pyrazine is reacted with N-bromo- or N-iodosuccinimide in a suitable inert solvent, such as DCM, under suitable reaction conditions, such as a convenient temperature, typically ranging between −10 °C. and 60° C. for a period of time to ensure the completion of the reaction. Step H can be performed by reacting a compound of Formula (IV) with morpholine in a suitable inert solvent, such as CH$_3$CN, under suitable reaction conditions, such as heating at a convenient temperature, either by conventional heating or under microwave irradiation for a period of time to ensure the completion of the reaction. A particular example of step H is described herein below for the synthesis of intermediate A8.

Experimental Procedure 3

The intermediate compound according to Formula (IIIa), can be prepared following the reaction steps shown in the reaction scheme (3) below Reaction Scheme 3

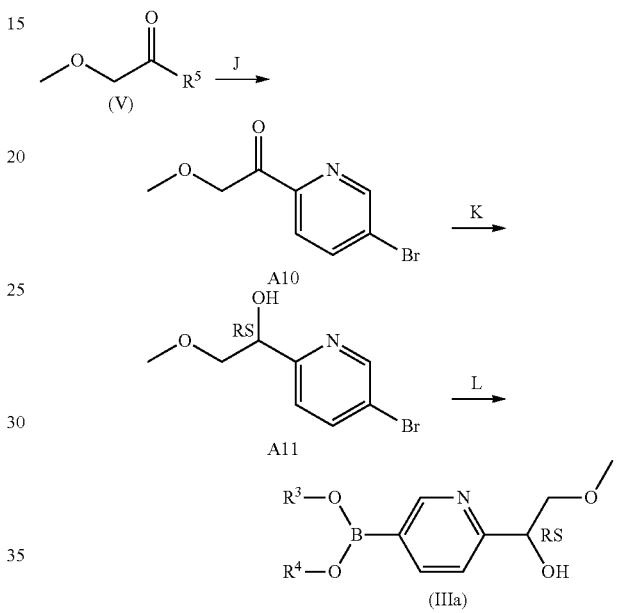

J: Ketone formation
K: Ketone reduction
L: Boronic acid or boronic ester formation Compounds of Formula (IIIa) in the above reaction scheme (3), wherein R$^3$ and R$^4$ may be hydrogen or C$_{1-4}$alkyl, or may be taken together to form for example a bivalent radical of Formula —CH$_2$—CH$_2$—, —CH$_2$—CH$_2$—CH$_2$—, or —C(CH$_3$)$_2$C(CH$_3$)$_2$—, can be prepared from commercially available materials via a three step (steps J, K, L) procedure, described hereinbelow.

In step J, a compound of Formula A10 can be prepared by reacting a compound of Formula (V) with a suitable reagent such as Grignard reagent derived from 5-bromo-2-iodopyridine, and for example a C$_{1-4}$alkylmagnesium halide reagent, such as for example isopropylmagnesium chloride, under reaction conditions that are known to the skilled person, such as in THF at 0° C. under an inert atmosphere. Compounds of Formula (V), wherein R$^5$ may be selected for example, from optionally substituted —O—C$_{1-4}$alkyl, —N(C$_{1-4}$alkyl)(OC$_{1-4}$alkyl), —O-aryl and forms, together with the (C=O) group an activated carbonyl compound, such as for example an ester or an amide, such as for example a Weinreb amide, can be obtained commercially or be prepared according to reaction conditions known to the skilled person, such as those described below in the synthesis of intermediate A9.

In step K, a compound of Formula A11 can be prepared by reacting an intermediate of Formula A10 with a reducing reagent such as sodium borohydride in a suitable inert solvent such as methanol, under suitable reaction conditions, such as a convenient temperature, typically ranging between −10° C. and 25° C. A particular example of step K is described hereinbelow for the synthesis of intermediate A11.

In step L, a compound of Formula (IIIa) can be prepared by reacting an intermediate of Formula A11 with an appropriate tri-$C_{1-4}$alkylborate, such as triisopropyl borate, in the presence of a suitable base, such as n-butyllithium in a suitable inert solvent such as $Et_2O$, under suitable reaction conditions, such as a convenient temperature, typically ranging between −78° C. and 25° C., alternatively, a compound of Formula (IIIa) can be prepared by reacting an intermediate of Formula A8 with an appropriate dioxaborolane derivative, such as for example, 4,4,4',4',5,5,5',5'-octamethyl-2,2'-bi-1,3,2-dioxaborolane, in the presence of a suitable base, such as potassium acetate, in a suitable solvent such as 1,4-dioxane, in the presence of a palladium catalyst, such as [1,1'-bis(diphenylphosphino)ferrocene]dichloropalladium(II), under suitable reaction conditions, such as a convenient temperature ranging from 60 to 100° C. A particular example of step L is described hereinbelow for the synthesis of intermediate A12.

Experimental Procedure 4

The intermediate compound according to Formula (IIIb), can be prepared following the reaction steps shown in the reaction scheme (4) below Reaction Scheme 4

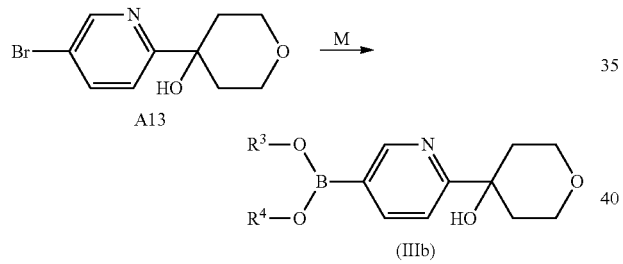

(IIIb)

M: Boronic acid or boronic ester formation

Compounds of Formula (IIIb) in the above reaction scheme (4), wherein $R^3$ and $R^4$ may be hydrogen or $C_{1-4}$alkyl, or may be taken together to form for example a bivalent radical of Formula —$CH_2$—$CH_2$—, —$CH_2$—$CH_2$—$CH_2$—, or —$C(CH_3)_2C(CH_3)_2$—, can be prepared from commercially available materials via a one step procedure, described hereinbelow.

In step M, a compound of Formula (IIIb) can be prepared by reacting an intermediate of Formula A13 with an appropriate tri-$C_{1-4}$alkylborate, such as triisopropyl borate, in the presence of a suitable base, such as n-butyllithium in a suitable inert solvent such as $Et_2O$, under suitable reaction conditions, such as a convenient temperature, typically ranging between −78° C. and 25° C., alternatively, a compound of Formula (IIIb) can be prepared by reacting an intermediate of Formula A13 with an appropriate dioxaborolane derivative, such as for example, 4,4,4',4',5,5,5',5'-octamethyl-2,2'-bi-1,3,2-dioxaborolane, in the presence of a suitable base, such as potassium acetate, in a suitable solvent such as 1,4-dioxane, in the presence of a palladium catalyst, such as [1,1'-bis(diphenylphosphino)ferrocene]dichloropalladium(II), under suitable reaction conditions, such as a convenient temperature ranging from 60 to 100° C. A particular example of step L is described hereinbelow for the synthesis of intermediate A14.

The compound of Formula A13 [CAS 1206912-74-4] and the boronic acid thereof [CAS 1207759-01-0] are known in the art. An exemplary procedure for the synthesis of A13 by reaction of 2,5-dibromopyridine with tetrahydro-4H-pyran-4-one is described herein below.

Experimental Procedure 5a

From the above, it follows that, particular compounds of Formula (I), wherein the substituent —$CR'R^2(OH)$ is

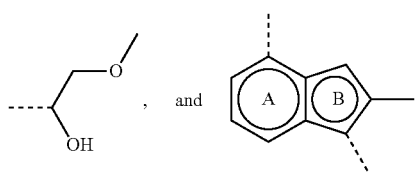

is a bicycle of Formula a)

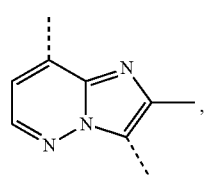

herein referred to as (I'-a), can be prepared by reacting a compound of Formula (IIa) and a compound of Formula (IIIa), under the reaction conditions described hereinabove in Experimental procedure 1.

Reaction Scheme 5a

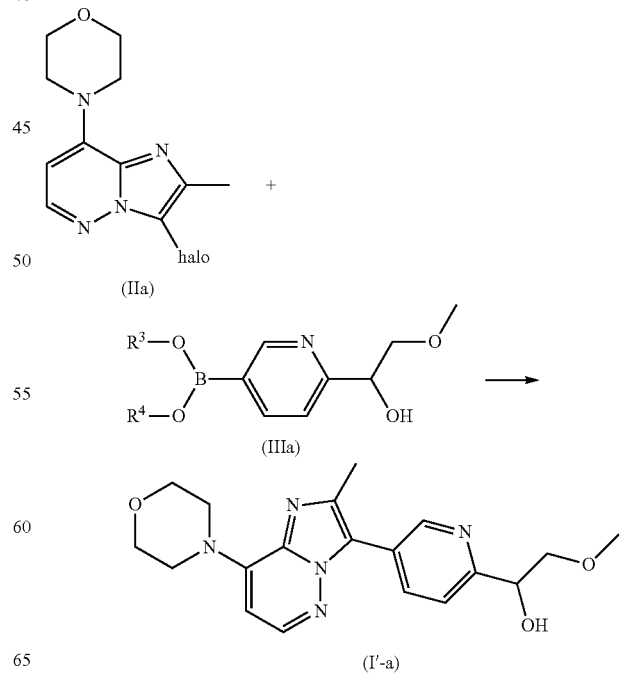

Experimental Procedure 5b

Likewise, a compound of Formula (I), wherein the substituent —CR'R²(OH) is

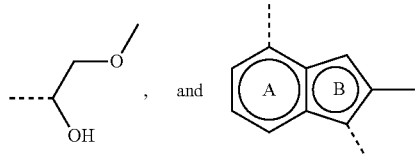

, and is a bicycle of Formula b)

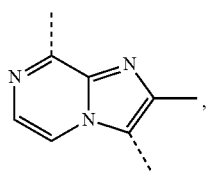

, herein referred to as (I'-b), can be prepared by reacting a compound of Formula (IIb) and a compound of Formula (IIIa), under the reaction conditions described herein above in Experimental procedure 1.

Reaction Scheme 5b

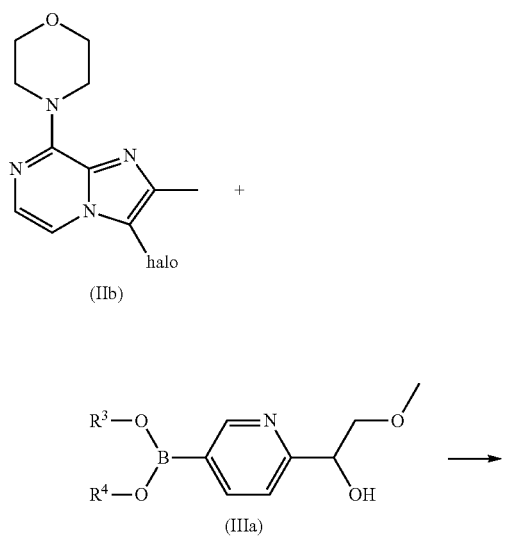

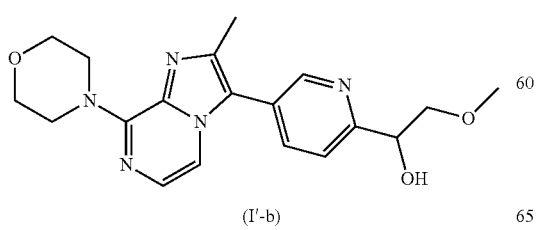

(I'-b)

Experimental Procedure 5c

From the above, it follows that particular compounds of Formula (I) wherein the substituent —CR'R²(OH) is

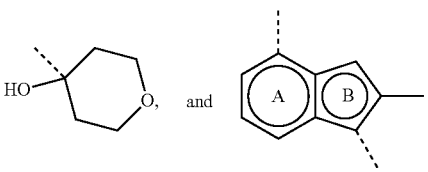

and is a bicycle of Formula a)

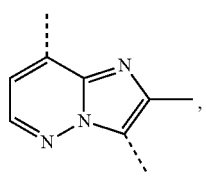

, herein referred to as (I''-a), can be prepared by reacting a compound of Formula (IIa) and a compound of Formula (IIIb), under the reaction conditions described hereinabove in Experimental procedure 1.

Reaction Scheme 5c

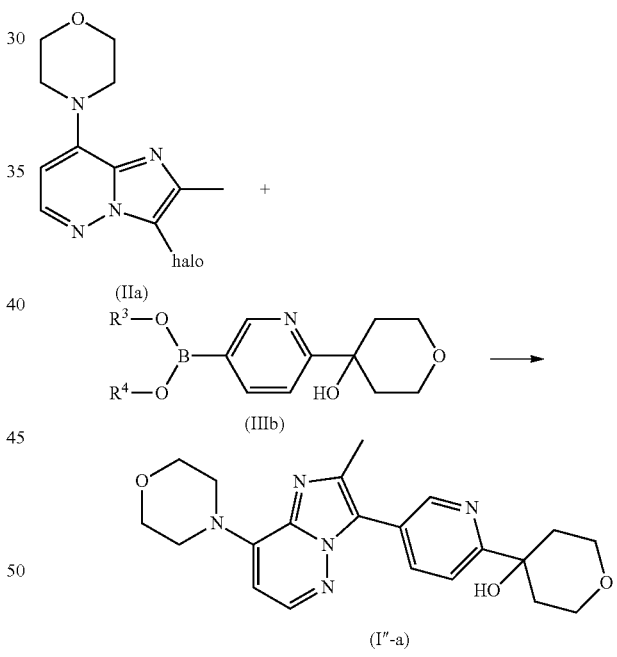

Experimental Procedure 5d

From the above, it follows that particular compounds of Formula (I) wherein the substituent —CR'R²(OH) is

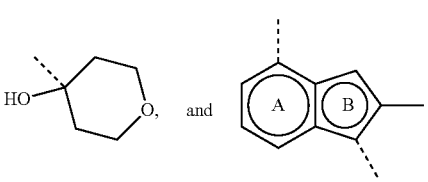

is a bicycle of Formula b)

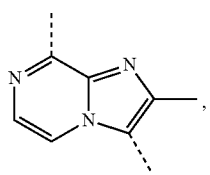

herein referred to as (I″-b), can be prepared by reacting a compound of Formula (IIb) and a compound of Formula (IIIb), under the reaction conditions described hereinabove in Experimental procedure 1.

Reaction Scheme 5d

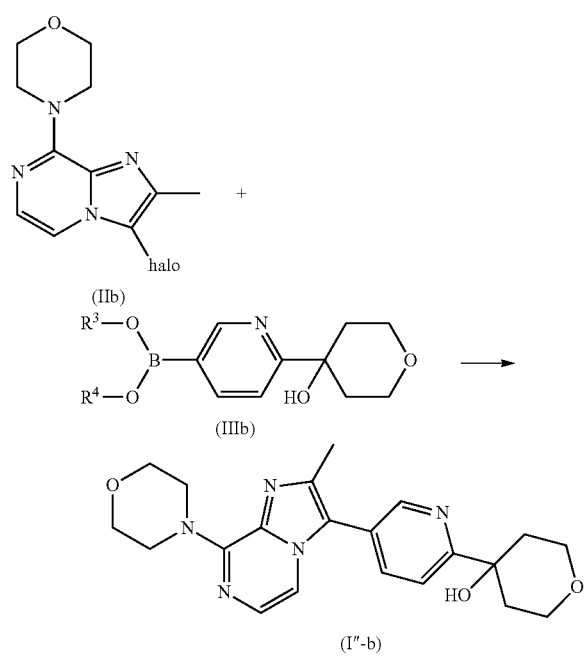

Pharmacology

The compounds according to the invention inhibit PDE10 enzyme activity, in particular PDE10A enzyme activity and hence raise the levels of cAMP or cGMP within cells that express PDE10. Accordingly, inhibition of PDE10 enzyme activity may be useful in the treatment of diseases caused by deficient amounts of cAMP or cGMP in cells. PDE10 inhibitors may also be of benefit in cases in which raising the amount of cAMP or cGMP above normal levels results in a therapeutic effect. Thus, inhibitors of PDE10 may be used to treat disorders of the peripheral and central nervous system, cardiovascular diseases, cancer, gastro-enterological diseases, endocrinological or metabolic diseases and urological diseases.

Hence, the present invention relates to a compound according to the present invention for use as a medicine, as well as to the use of a compound according to the invention or a pharmaceutical composition according to the invention for the manufacture of a medicament. The present invention also relates to a compound according to the present invention or a pharmaceutical composition according to the invention for use in the treatment or prevention of, in particular treatment of, a condition in a mammal, including a human, the treatment or prevention of which is affected or facilitated by the inhibition of phosphodiesterase 10 enzyme. The present invention also relates to the use of a compound according to the present invention or a pharmaceutical composition according to the invention for the manufacture of a medicament for the treatment or prevention of, in particular treatment of, a condition in a mammal, including a human, the treatment or prevention of which is affected or facilitated by the inhibition of phosphodiesterase 10 enzyme.

The present invention also relates to a compound according to the invention, or a pharmaceutical composition according to the invention for use in the treatment, prevention, amelioration, control or reduction of the risk of various neurological, psychiatric and metabolic disorders associated with phosphodiesterase 10 dysfunction in a mammal, including a human, the treatment or prevention of which is affected or facilitated by the inhibition of phosphodiesterase 10.

Also, the present invention relates to the use of a compound according to the invention or a pharmaceutical composition according to the invention for the manufacture of a medicament for treating, preventing, ameliorating, controlling or reducing the risk of various neurological and psychiatric disorders associated with phosphodiesterase 10 dysfunction in a mammal, including a human, the treatment or prevention of which is affected or facilitated by the inhibition of phosphodiesterase 10.

Where the invention is said to relate to the use of a compound or composition according to the invention for the manufacture of a medicament for e.g. the treatment of a subject, such as a mammal, in particular a human, it is understood that such use is to be interpreted in certain jurisdictions as a method of e.g. treatment of a subject, such as a mammal, in particular a human, comprising administering to a subject in need of such e.g. treatment, an effective amount of a compound or composition according to the invention.

In particular, the indications that may be treated with PDE10 inhibitors, either alone or in combination with other drugs, include, but are not limited to, those diseases thought to be mediated in part by the basal ganglia, prefrontal cortex and hippocampus.

These indications include neurological and psychiatric disorders selected from psychotic disorders and conditions; anxiety disorders; movement disorders; drug abuse; mood disorders; neurodegenerative disorders; cognitive disorders; pain; autistic disorders; and metabolic disorders.

In particular, the psychotic disorders and conditions associated with PDE10 dysfunction include one or more of the following conditions or diseases: schizophrenia, for example of the paranoid, disorganized, catatonic, undifferentiated or residual type; schizophreniform disorder; schizoaffective disorder, such as delusional or depressive type; delusional disorder; substance-induced psychotic disorder such as psychosis induced by alcohol, amphetamine, cannabis, cocaine, hallucinogens, inhalants, opioids, or phencyclidine; personality disorders of the paranoid type; and personality disorder of the schizoid type.

In particular, the anxiety disorders include panic disorder; agoraphobia; specific phobia; social phobia; obsessive-compulsive disorder; post-traumatic stress disorder; acute stress disorder; and generalized anxiety disorder.

In particular, movement disorders include Huntington's disease and dyskinesia; Parkinson's disease; restless leg syndrome and essential tremor. Additionally, Tourette's syndrome and other tic disorders can be included.

In particular, the central nervous system disorder is a substance-related disorder selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

In particular, mood disorders and mood episodes include depression, mania and bipolar disorders. Preferably, the mood disorder is selected from the group of bipolar disorders (I and II), cyclothymic disorder, depression, dysthymic disorder, major depressive disorder, treatment-resistant depression and substance-induced mood disorder.

In particular, neurodegenerative disorders include Parkinson's disease; Huntington's disease; dementia such as for example Alzheimer's disease; multi-infarct dementia; AIDS-related dementia or frontotemperal dementia. The neurodegenerative disorder or condition comprises dysfunction of striatal medium spiny neurons responses.

In particular, the central nervous system disorder is a cognitive disorder selected from the group of delirium, substance-induced persisting delirium, dementia, dementia of the Alzheimer's type, vascular dementia, dementia due to HIV disease, dementia due to intracranial tumours, cerebral trauma or head trauma, dementia due to stroke, dementia due to Parkinson's disease, dementia due to Huntington's disease, dementia due to Pick's disease, dementia due to Creutzfeldt-Jakob Disease, dementia due to Lewy body disease, substance-induced persisting dementia, dementia due to multiple etiologies, dementia not otherwise specified, mild cognitive impairment, age-related cognitive impairment, senility, amnestic disorder, post-traumatic stress disorder, mental retardation, learning disorder, attention-deficit/hyperactivity disorder (ADHD), and Down's syndrome.

In particular, pain includes acute and chronic states, severe pain, intractable pain, neuropathic pain and post-traumatic pain.

In particular, the central nervous system disorder is autistic disorder or autism.

In particular, metabolic disorders include diabetes, in particular type 1 or type 2 diabetes, and related disorders such as obesity. Additional related disorders include syndrome X, impaired glucose tolerance, impaired fasting glucose, gestational diabetes, maturity-onset diabetes of the young (MODY), latent autoimmune diabetes adult (LADA), associated diabetic dyslipidemia, hyperglycemia, hyperinsulinemia, dyslipidemia, hypertriglyceridemia, and insulin resistance.

Additionally, the growth of some cancer cells is inhibited by cAMP and cGMP, the compounds of the invention may be useful in the treatment of cancer, such as renal carcinoma and breast cancer.

Preferably, the psychotic disorder is selected from the group of schizophrenia, delusional disorder, schizoaffective disorder, schizophreniform disorder and substance-induced psychotic disorder.

Preferably, the central nervous system disorder is a personality disorder selected from the group of obsessive-compulsive personality disorder and schizoid, schizotypal disorder.

Preferably, the central nervous system disorder is a mood disorder selected from the group of bipolar disorders (I & II), cyclothymic disorder, depression, dysthymic disorder, major depressive disorder, treatment-resistant depression and substance-induced mood disorder.

Preferably, the central nervous system disorder is attention-deficit/hyperactivity disorder.

Preferably, the central nervous system disorder is a cognitive disorder selected from the group of delirium, substance-induced persisting delirium, dementia, dementia of the Alzheimer's type, vascular dementia, dementia due to HIV disease, dementia due to head trauma, dementia due to stroke, dementia due to Parkinson's disease, dementia due to Huntington's disease, dementia due to Pick's disease, dementia due to Creutzfeldt-Jakob Disease, dementia due to Lewy body disease, substance-induced persisting dementia, dementia due to multiple etiologies, dementia not otherwise specified, mild cognitive impairment, senility, and Down's syndrome.

Other central nervous system disorders include schizoanxiety disorder, and comorbid depression and anxiety, in particular major depressive disorder with comorbid generalized anxiety disorder, social anxiety disorder, or panic disorder; it is understood that comorbid depression and anxiety may also be referred to by the terms anxious depression, mixed anxiety depression, mixed anxiety-depressive disorder, or major depressive disorder with anxiety symptoms, which are used indistinctively herein.

Preferably the disorders treated by the compounds of the present invention are selected from schizophrenia, obsessive-compulsive disorder, generalized anxiety disorder, Huntington's disease, dyskinesia, Parkinson's disease, depression, bipolar disorders, dementia such as Alzheimer's disease, attention-deficit/hyperactivity disorder, drug abuse, pain, diabetes and obesity.

Of the disorders mentioned above, the treatment of anxiety, obsessive-compulsive disorder, schizophrenia, depression, attention-deficit/hyperactivity disorder, Alzheimer's disease, Huntington's disease and diabetes are of particular importance.

Preferably, the disorders treated by the compounds of the present invention are schizophrenia, including positive and negative symptoms thereof, and cognitive deficits, such as impaired attention or memory.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Therefore, the invention also relates to a compound according to the invention, for use in the treatment of any one of the diseases mentioned hereinbefore.

The invention also relates to a compound according to the invention for use in treating any one of the diseases mentioned hereinbefore.

The invention also relates to a compound according to the invention, for the treatment or prevention, in particular treatment, of any one of the diseases mentioned hereinbefore.

The invention also relates to the use of a compound according to the invention, for the manufacture of a medicament for the treatment or prevention of any one of the disease conditions mentioned hereinbefore.

The invention also relates to the use of a compound according to the invention for the manufacture of a medicament for the treatment of any one of the disease conditions mentioned hereinbefore.

The compounds of the present invention can be administered to mammals, preferably humans, for the treatment or prevention of any one of the diseases mentioned hereinbefore.

In view of the utility of the compounds according to the invention, there is provided a method of treating warm-blooded animals, including humans, suffering from any one of the diseases mentioned hereinbefore, and a method of preventing in warm-blooded animals, including humans, any one of the diseases mentioned hereinbefore.

Said methods comprise the administration, i.e. the systemic or topical administration, preferably oral administration, of a therapeutically effective amount of a compound according to the invention to warm-blooded animals, including humans.

Therefore, the invention also relates to a method of treating or preventing a disorder mentioned hereinbefore comprising administering to a subject in need thereof, a therapeutically effective amount of any of the compounds or a therapeutically effective amount of pharmaceutical compositions described herein.

The compounds according to the present invention described herein can be used alone, in combination or in combination with other pharmaceutical agents such as other agents used in the treatment of psychoses, such as schizophrenia and bipolar disorder, obsessive-compulsive disorder, Parkinson's disease, cognitive impairment and/or memory loss, e.g. nicotinic α-7 agonists and positive allosteric modulators, PDE4 inhibitors, other PDE10 inhibitors, calcium channel blockers, muscarinic M1 and M2 modulators, adenosine receptor modulators, ampakines, NMDA-R modulators, mGluR modulators, dopamine modulators, serotonin modulators, cannabinoid modulators, and cholinesterase inhibitors (e.g. donepezil, rivastigmine, and galantamine). In such combinations, the compounds of the present invention may be utilized in combination with one or more other drugs in the treatment, prevention, control, amelioration, or reduction of risk of diseases or conditions for which compounds of Formula (I) and the stereoisomeric forms thereof, and the pharmaceutically acceptable salts and solvates thereof, or the other drugs may have utility, where the combination of the drugs together are safer or more effective than either drug alone.

One skilled in the art will recognize that a therapeutically effective amount of the compounds of the present invention is the amount sufficient to inhibit the PDE10 enzyme and that this amount varies inter alia, depending on the type of disease, the concentration of the compound in the therapeutic formulation, and the condition of the patient. Generally, an amount of PDE10 inhibitor to be administered as a therapeutic agent for treating diseases in which inhibition of the PDE10 enzyme is beneficial, such as the disorders described herein, will be determined on a case by case by an attending physician.

Generally, a suitable dose is one that results in a concentration of the PDE10 inhibitor at the treatment site in the range of 0.5 nM to 200 µM, and more usually 5 nM to 50 µM.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, more preferably from about 0.01 mg/kg to about 2.50 mg/kg, even more preferably from about 0.01 mg/kg to about 1 mg/kg, more preferably from about 0.05 mg/kg to about 1 mg/kg body weight and most preferably from about 0.1 mg/kg to about 0.5 mg/kg body weight. The amount of a compound according to the present invention, also referred to here as the active ingredient, which is required to achieve a therapeutical effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

Pharmaceutical Compositions

The present invention also provides compositions for preventing or treating diseases in which inhibition of the PDE10 enzyme may be beneficial, such as the disorders described herein. While it is possible for the active ingredient to be administered alone, it is preferable to present it as a pharmaceutical composition. Accordingly, the present invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable salt thereof, a solvate thereof or a stereochemically isomeric form thereof The carrier or diluent must be "acceptable" in the sense of being compatible with the other ingredients of the composition and not deleterious to the recipients thereof The compounds according to the invention, in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). To prepare the pharmaceutical compositions of this invention, a therapeutically effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for oral, topical (for example via a nose spray, eye drops or via a cream, gel, shampoo or the like), rectal or percutaneous administration, by parenteral injection or by inhalation, such as a nose spray. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are employed. For parenteral compositions, the carrier will usually comprise sterile water, at least in large part, though other ingredients, for example, surfactants to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, said additives do not introduce a significant deleterious effect on the skin. Said additives may facilitate the administration to the skin and/or may be helpful for preparing the desired compositions. These compositions may be administered in various ways, e.g., as a transdermal patch, as a spot-on treatment, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, teaspoonfuls, tablespoonfuls, and segregated multiples thereof Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The exact dosage and frequency of administration depends on the particular compound of Formula (I) or stereoisomeric form thereof, or pharmaceutically acceptable salt or solvate thereof used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound of Formula (I) or stereoisomeric form thereof, or pharmaceutically acceptable salt or solvate thereof, that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

As already mentioned, the invention also relates to a pharmaceutical composition comprising the compounds according to the invention and one or more other drugs for use as a medicament or for use in the treatment, prevention, control, amelioration, or reduction of risk of diseases or conditions for which compounds of Formula (I) and stereoisomeric forms thereof, and pharmaceutically acceptable salts and solvates thereof, or the other drugs may have utility as well. The use of such a composition for the manufacture of a medicament, as well as the use of such a composition for the manufacture of a medicament in the treatment, prevention, control, amelioration or reduction of risk of diseases or conditions for which compounds of Formula (I) and stereoisomeric forms thereof, and pharmaceutically acceptable salts and solvates thereof, or the other drugs may have utility are also contemplated. The present invention also relates to a combination of a compound according to the present invention and an additional pharmaceutical agent. The present invention also relates to such a combination for use as a medicine. The present invention also relates to a product comprising (a) a compound according to the present invention, a pharmaceutically acceptable salt thereof or a solvate thereof, and (b) an additional pharmaceutical agent, as a combined preparation for simultaneous, separate or sequential use in the treatment or prevention of a condition in a mammal, including a human, the treatment or prevention of which is affected or facilitated by the effect of PDE10 inhibitors, in particular PDE10A inhibitors. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

Chemistry

Several methods for preparing the compounds of this invention are illustrated in the following examples. Unless otherwise noted, all starting materials were obtained from commercial suppliers and used without further purification.

Hereinafter, "DCM" means dichloromethane, "DIPE" means diisopropylether, "DMF" means N,N-dimethylformamide, "Et₂O" means diethylether, "h" means hour(s), "LCMS" means liquid chromatography mass spectrometry, "MeCN" means acetonitrile, "MeOH" means methanol, "min" means minute(s), "mp" means melting point, "MS" means mass spectrometry, "Pd(PPh₃)₄" means tetrakis(triphenylphosphine)palladium (0), "RT" or "r.t." means room temperature, "sat." means saturated, "SFC" means supercritical fluid chromatography, "THF" means tetrahydrofuran.

Thin layer chromatography (TLC) was carried out on silica gel 60 F254 plates (Merck) using reagent grade solvents. Open column chromatography was performed on silica gel, particle size 60 Å, mesh=230-400 (Merck) using standard techniques. Automated flash column chromatography was performed using ready-to-connect cartridges from Merck, on irregular silica gel, particle size 15-40 μm (normal phase disposable flash columns) on a SPOT system from Armen Instrument.

A. Preparation of the Intermediates

EXAMPLE A1

Intermediate 1

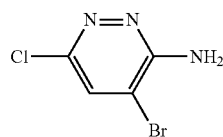

To a solution of 3-amino-6-chloropyridazine ([CAS 5469-69-2], (200 g, 1538 mmol) and NaHCO₃ (258 g, 3076 mmol) in CH₃OH (2000 mL) was added Br₂ ([CAS 7726-95-6], 369 g, 2308 mmol) dropwise at 0° C. and the mixture was stirred overnight at room temperature.

Then water (2000 mL) was added and the solid precipitate was filtered and washed with water. The solid was dried under vacuum to give intermediate 1 (260 g, 81.7%).

EXAMPLE A2

Intermediate 2

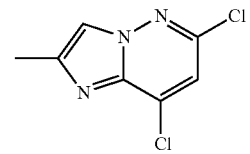

Intermediate 1 (225 g, 1082 mmol) and chloro-2-propanone ([CAS 78-95-5], 478 g, 5410 mmol) were added into DMF (1500 mL) and stirred for 2 h at 100 ° C. Then the reaction mixture was concentrated under reduced pressure. Water (2000 mL) was added, and the mixture was extracted with CH₂Cl₂ (3×2000 mL). The organic layer was dried over Na₂SO₄, filtered and the solvent was evaporated under reduced pressure to yield 250 g of intermediate 2, which was used without further purification.

EXAMPLE A3

Intermediate 3

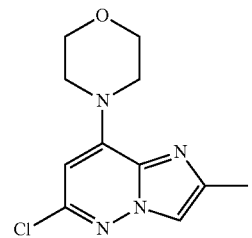 [SMILES: Cc1cn2nc(Cl)cc(N3CCOCC3)c2n1]

A mixture of intermediate 2 (250 g), morpholine ([CAS 110-91-8], 103 g, 1190 mmol) and N,N-diisopropylethylamine ([CAS 7087-68-5], 208.7 g, 1623 mmol) in CH₃CN (2000 mL) was refluxed for 5 h. Then, the reaction mixture was concentrated under reduced pressure and the residue was purified by column chromatography over silica gel (eluent: petroleum ether/ethyl acetate, 3/1) to give 70 g (22.4%) of intermediate 3 as a yellow solid.

EXAMPLE A4

Intermediate 4

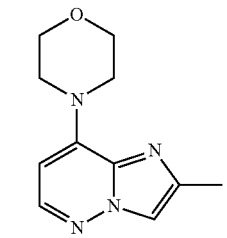 [SMILES: Cc1cn2nccc(N3CCOCC3)c2n1]

To a solution of intermediate 3 (70 g, 277 mmol) in CH₃OH (1000 mL) was added palladium on carbon (7 g)

and the mixture was stirred at room temperature under hydrogen (30 psi; 206.84 kPa) for 10 h. After uptake of hydrogen (1 equiv), the catalyst was filtered off and the solvent was evaporated under reduced pressure. Then the residue was dissolved in CH$_2$Cl$_2$ (500 mL) and washed with a saturated NaHCO$_3$ aqueous solution. The organic layer was separated, dried over Na$_2$SO$_4$, and evaporated under reduced pressure to yield 49 g (81%) of intermediate 4.

mp=137.2-138.3° C.

EXAMPLE A5

Intermediate 5

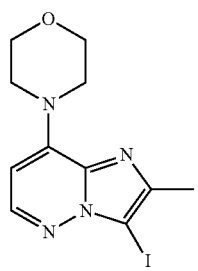 [SMILES: Cc1nc2c(N3CCOCC3)ccnn2c1I]

N-Iodosuccinimide ([CAS 516-12-1], 97.413 g, 432.973 mmol) was added portionwise to a mixture of intermediate 4 (90 g, 412.355 mmol), CH$_2$Cl$_2$ (3840 mL) and acetic acid (153 mL) at 0° C., and the resulting mixture was stirred at 0° C. over 1 h. The resulting mixture was washed with a Na$_2$S$_2$O$_3$ aqueous solution (10%) and a Na$_2$CO$_3$ saturated aqueous solution and the aqueous layer was further extracted with CH$_2$Cl$_2$. The combined organic layer was dried (Na$_2$SO$_4$), filtered and evaporated in vacuo. The crude product was triturated with MeOH and the precipitate was filtered and washed with Et$_2$O to yield 108.279 g (76.3%) of intermediate 5 as a white solid.

EXAMPLE A6

Intermediate 6

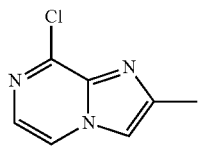

A mixture of 3-chloro-pyrazin-2-ylamine (48.7 g, 375 8 mmol) and chloroacetone (120 ml, 1504.5 mmol) was stirred at 90 °C. for 16 h. in a sealed tube protected from light. After cooling to RT, Et$_2$O was added and the solid formed was filtered off, washed with further Et$_2$O, suspended in a saturated solution of sodium carbonate and extracted with DCM. The organic layer was separated, dried (Na$_2$SO$_4$), filtered and the solvents evaporated in vacuo. The crude product was precipitated from Et$_2$O to yield intermediate 6 (43.2 g, 68%) as a white solid which was used in the next step without further purification. m.p. 133.5-138.6° C. (WRS-2A).

EXAMPLE A7

Intermediate 7

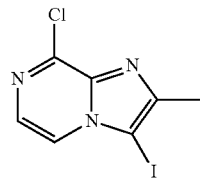

N-Iodosuccinimide (14.1 g, 62 mmol) was added to a stirred solution of intermediate 6 (9.58 g, 57 mmol) in a mixture of DCM and acetic acid at 0° C. The mixture was allowed to warm to RT and then stirred for 16 h. The mixture was diluted with further DCM and washed with a saturated solution of sodium carbonate and sodium thiosulfite. The organic layer was separated, dried (Na$_2$SO$_4$), filtered and the solvents evaporated in vacuo. The crude product was precipitated from diisopropyl ether to yield intermediate 7 (16 g, 97%) as a pale brown solid which was used in the next step without further purification.

EXAMPLE A8

Intermediate 8

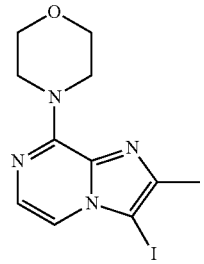 [SMILES: Cc1nc2c(N3CCOCC3)nccn2c1I]

Morpholine (19.79 mL, 224.877 mmol) was added to a solution of intermediate 7 (33 g, 112.439 mmol) and DIPEA (48.963 mL, 281.097 mmol) in acetonitrile (300 mL), and the reaction mixture was stirred at reflux (100° C. drysyn™ heater) overnight. Then the mixture was cooled in an ice bath, the precipitated product filtered, rinsed with acetonitrile and dried, to yield 33.8 g (87%) of intermediate 8. m.p. 135.3-136.7° C. (WRS-2A).

EXAMPLE A9

Intermediate 9

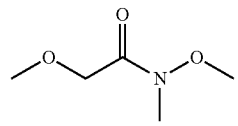

A mixture of methoxyacetic acid ([CAS 625-45-6], 200 g, 2220.30 mmol), N-methoxy-methanamine hydrochloride ([CAS 6638-79-5], 216.577 g, 2220.30 mmol), 1-hydroxy- 1H-benzotriazole (300.014 g. 2220.30 mmol), N-(3-dimethylaminopropyl)-N'-ethylcarbodiimide hydrochloride (344.682 g, 2220.300 mmol) and Et₃N (336.742 g, 3330.450 mmol) in CH₂Cl₂ (6000 mL) was stirred at room temperature overnight. The mixture was then washed with a saturated NaHCO₃ aqueous solution and a 10% citric acid aqueous solution.

The organic layer was dried (Na₂SO₄) and concentrated under vacuum to yield 150 g (50.1%) of intermediate 9.

EXAMPLE A10

Intermediate 10

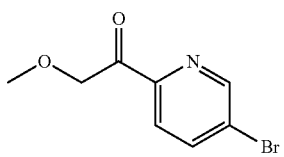

A mixture of 5-bromo-2-iodo-pyridine ([CAS 223463-13-6], 140 g, 493.145 mmol) and THF (2500 mL) was stirred at 0° C. under N₂. An isopropylmagnesium chloride solution (2.0 M in THF, [CAS 1068-55-9], 246.572 mL, 493.145 mmol) was then added at 0° C. and the resulting mixture was stirred at 0° C. for 0.5 h. Intermediate 9 (72.226 g, 542.460 mmol) was then added dropwise and the mixture was stirred at 0° C. for 1 h. The reaction was quenched by addition of HCl (1 M) to pH 2 and stirred for 0.5 h. Then to this mixture was added NaOH (1M) to pH 11 and the mixture was extracted with ethyl acetate. The organic layer was concentrated under vacuum and the residue was purified by flash column chromatography over silica gel (eluent: petroleum ether/ethyl acetate, 8/1). The desired fractions were collected and the solvent was evaporated to give 49 g (43.2%) of intermediate 10.

EXAMPLE A11

Intermediate 11

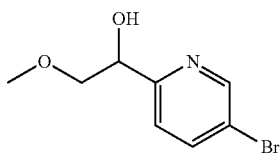

To a stirred solution of intermediate 10 (98 g, 425.978 mmol) in CH₃OH (700 mL) at 0° C. was added NaBH₄ (16.200 g, 425.978 mmol) portionwise and the mixture was stirred at 0° C. for 20 min. The reaction was then quenched with ethyl acetate, the solvent was removed under vacuum and to the resulting residue was added saturated aqueous ammonium chloride. The mixture was extracted with ethyl acetate, and the organic was concentrated under vacuum to afford 87.9 g (87.5%) of intermediate 11.

EXAMPLE A12

Intermediate 12

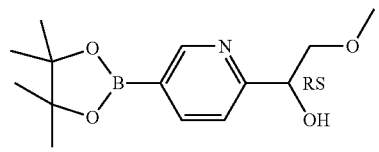

A mixture of intermediate 11 (37.5 g, 161.584 mmol), 4,4,4',4',5,5,5',5'-octamethyl-2,2'-bi-1,3,2-dioxaborolane ([CAS 73183-34-3], 65.653 g, 258.535 mmol) and potassium acetate (55.504 g, 565.545 mmol) in 1,4-dioxane (750.532 mL) was flushed with N₂ for a few minutes. Then [1,1'-bis(diphenylphosphino)ferrocene]dichloropalladium (II) (11.823 g, 16.158 mmol) was added and the reaction mixture was stirred at 85° C. for 55 min. The resulting mixture was used without further manipulation in the subsequent reaction step.

EXAMPLE A13

Intermediate 13

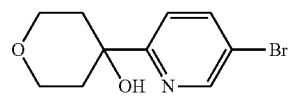

Butyllithium (2.5 M in hexanes, 20.262 mL, 50.656 mmol) was added dropwise to a stirred solution of 2,5-dibromopyridine ([CAS 624-28-2], 10 g, 42.213 mmol) in toluene (400 mL) under nitrogen at −78° C. The mixture was stirred at −78° C. for 2 h. Then, tetrahydro-4H-pyran-4-one ([CAS 29943-42-8], 4.869 mL, 52.766 mmol) was added dropwise and the mixture was stirred at −78° C. for 1 h. The mixture was quenched with sat. aqueous NH₄Cl and it was allowed to warm to r.t. The organic layer was separated, washed with sat. NaHCO₃, sat. NaCl, dried (Na₂SO₄), filtered and concentrated in vacuo. The residue was purified by flash column chromatography (silica; EtOAc in heptane 0/100 to 30/70) in two different batches. The desired fractions were collected and the solvents concentrated in vacuo to yield 5.21 g (48%) of intermediate 13 as white solid.

EXAMPLE A14

Intermediate 14

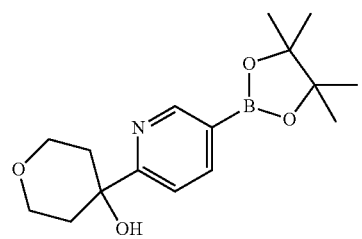 [SMILES: CC1(C)OB(c2ccc(C3(O)CCOCC3)nc2)OC1(C)C]

[1,1'-Bis(diphenylphosphino)ferrocene]dichloropalladium(II) ([CAS 72287-26-4], 70.871 mg, 0.0969 mmol) was added to a stirred suspension of intermediate 13, 4,4,4',4', 5,5,5',5'-octamethyl-2,2'-bi-1,3,2-dioxaborolane ([CAS 73183-34-3], 639.492 mg, 2.518 mmol), and potassium acetate (570.3 mg, 5.8 mmol) in 1,4-dioxane (4.47 mL) under nitrogen. The mixture was stirred at 85° C. for 30 min to yield intermediate 14, which was used in the next step without further purification.

B. Preparation of the Final Compounds

EXAMPLE B1

2-Methoxy-1-[5-(2-methyl-8-morpholin-4-ylimidazo[1,2-b]pyridazin-3-yl)pyridin-2-yl]ethanol (Compound 1)

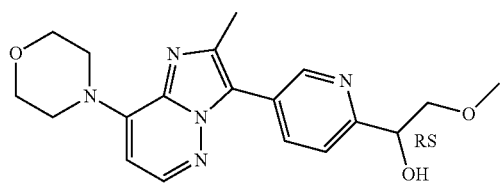 [SMILES: COCC(O)c1ccc(-c2c(C)nc3c(N4CCOCC4)ccnn23)cn1]

To a mixture of crude intermediate 12 (45 g, 161.207 mmol) in 1,4-dioxane (750 mL) (the mixture obtained in example A12), intermediate 5 (66.576 g, 193.449 mmol) and saturated Na$_2$CO$_3$ aqueous solution (52 mL) were added and flushed with N$_2$ for a few minutes. Pd(PPh$_3$)$_4$ (0.03 eq) was added and the reaction mixture was stirred at 85° C. for 24 h. Then additional Pd(PPh$_3$)$_4$ (0.01 eq) and saturated aqueous Na$_2$CO$_3$ solution (20 mL) were added and the reaction mixture was stirred at 85° C. for 24 h. The mixture was then partitioned between CH$_2$Cl$_2$ and water and extracted. The organic layers were dried (Na$_2$SO$_4$), filtered and evaporated. The crude was purified by flash column chromatography (silica; a 7M solution of ammonia in methanol in CH$_2$Cl$_2$ (10%) in EtOAc 0/100 to 80/20). The desired fractions were collected and the solvents evaporated in vacuo. The product was triturated with CH$_3$CN and filtered to yield 37.3 g (62.6%) of compound 1.

EXAMPLE B2

2-Methoxy-1-[5-(2-methyl-8-morpholin-4-ylimidazo[1,2-a]pyrazin-3-yl)pyridin-2-yl]ethanol (Compound 2)

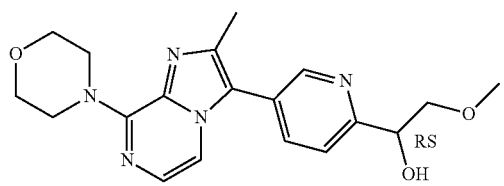 [SMILES: COCC(O)c1ccc(-c2c(C)nc3c(N4CCOCC4)nccn23)cn1]

A mixture of intermediate 8 (295.894 mg, 0.86 mmol) and intermediate 12 (240 mg, 0.86 mmol) in 1,4-dioxane (4 mL) and sat. Na$_2$CO$_3$ (0.85 mL) was flushed with N$_2$ for a few minutes. Then Pd(PPh$_3$)$_4$ (29.806 mg, 0.0258 mmol) was added and the mixture was stirred at 85 ° C. for 16 h. The mixture was diluted with water and extracted with CH$_2$Cl$_2$. The organic layer was separated, dried (Na$_2$SO$_4$), filtered and concentrated in vacuo. The residue was purified by flash column chromatography (silica; EtOAc 100% and then 7 M solution of ammonia in methanol in CH$_2$Cl$_2$ 10/90). The desired fractions were collected and concentrated in vacuo. The crude product was triturated with Et$_2$O to yield 95 mg (30%) of compound 2 as a pale brown solid.

EXAMPLE B3

4-[5-(2-Methyl-8-morpholin-4-ylimidazo[1,2-b]pyridazin-3-yl)pyridin-2-yl]tetrahydro-2H-pyran-4-ol (Compound 3)

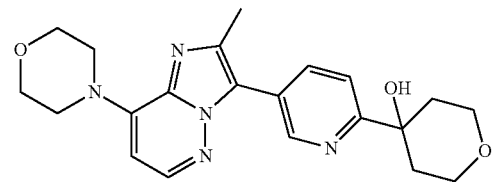 [SMILES: Cc1nc2c(N3CCOCC3)ccnn2c1-c1ccc(C2(O)CCOCC2)nc1]

A mixture of intermediate 5 (733.12 mg, 2.13 mmol) and intermediate 14 (591 mg, 1.937 mmol) in 1,4-dioxane (4.5 mL) and sat. aqueous Na$_2$CO$_3$ (2 mL) was flushed with N$_2$ for a few minutes. Then Pd(PPh$_3$)$_4$ (40.293 mg, 0.0349 mmol) was added and the mixture was stirred at 85° C. for 16 h. The mixture was diluted with water and extracted with CH$_2$Cl$_2$. The organic layer was separated, dried (Na$_2$SO$_4$), filtered and concentrated in vacuo. The residue was purified by flash column chromatography (silica; 7 M solution of ammonia in methanol in CH$_2$Cl$_2$ 0/100 to 4/96). The desired fractions were collected and concentrated in vacuo. The crude product was triturated with DIPE to yield 334 mg (44%) of compound 3 as a white solid.

EXAMPLE B4

4-[5-(2-Methyl-8-morpholin-4-ylimidazo[1,2-a]pyrazin-3-yl)pyridin-2-yl]tetrahydro-2H-pyran-4-ol (Compound 4)

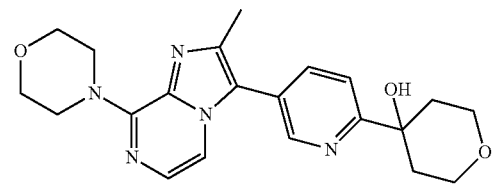 [SMILES: Cc1nc2c(N3CCOCC3)nccn2c1-c1ccc(C2(O)CCOCC2)nc1]

A mixture of intermediate 8 (400 mg, 1.162 mmol) and intermediate 14 (591 mg, 1.937 mmol) in 1,4-dioxane (4.5 mL) and sat. aqueous Na$_2$CO$_3$ (1 mL) was flushed with N$_2$ for a few minutes. Then Pd(PPh$_3$)$_4$ (40.293 mg, 0.0349 mmol) was added and the mixture was stirred at 85° C. for 16 h. The mixture was diluted with water and extracted with CH$_2$Cl$_2$. The organic layer was separated, dried (Na$_2$SO$_4$), filtered and concentrated in vacuo. The residue was purified by flash column chromatography (silica; 7 M solution of ammonia in methanol in CH$_2$Cl$_2$ 0/100 to 5/95). The desired fractions were collected and concentrated in vacuo. The crude product was triturated with MeCN to yield 202 mg (44%) of compound 4 as a pale grey solid.

Analytical Part

LCMS:

For (LC)MS-characterization of the compounds of the present invention, the following methods were used.

General Procedure A:

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified in the respective methods. Flow from the column was brought to the MS spectrometer. The MS detector was configured with an electrospray ionization source. Mass spectra were acquired on a single quadrupole SQD detector by scanning from 100 to 1000 in 0.1 second using an inter-channel delay of 0.08 second. The capillary needle voltage was 3.0 kV. The cone voltage was 25 V for positive ionization mode and 30 V for negative ionization mode. The source temperature was maintained at 140° C. Nitrogen was used as the nebulizer gas. Data acquisition was performed with MassLynx-Openlynx software.

Method 1:

In addition to the general procedure A: Reversed phase UPLC was carried out on a RRHD Eclipse Plus-C18 (1.8 μm, 2.1×50 mm) from Agilent, with a flow rate of 1.0 ml/min, at 50° C. The gradient conditions used are: 95% A (6.5 mM NH$_4$AcO in H$_2$O/MeCN 95/5), 5% B (MeCN), to 40% A, 60% B in 3.8 minutes, to 5% A, 95% B in 4.6 minutes, kept till 5.0 minutes. The injection volume was 2 μl.

General Procedure B:

The HPLC measurement was performed using an HP 1100 (Agilent Technologies) system comprising a binary pump with degasser, an autosampler, a column oven, a diode-array detector (DAD) and a column as specified in the respective methods below. Flow from the column was split to the MS spectrometer. The MS detector (TOF) was configured with an electrospray ionization source. Mass spectra were acquired on a Time of Flight (TOF, Waters) detector by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. The source temperature was maintained at 140° C. Nitrogen was used as the nebulizer gas. Data acquisition was performed with MassLynx-Openlynx software.

Method 2:

In addition to the general procedure B: Reversed phase HPLC was carried out on a Eclipse Plus-C18 column (3.5 μm, 2.1×30 mm) from Agilent, with a flow rate of 1.0 mL/min, at 60° C. The gradient conditions used are: 95% A (6.5 mM NH$_4$AcO in H$_2$O/MeCN 95/5), 5% B (MeCN/MeOH, 1/1) to 100% B in 5.0 min, kept till 5.15 min and equilibrated to initial conditions at 5.3 min until 7.0 min. the injection volume was 2 μL.

Melting Points:

Values are peak values or melt ranges, and are obtained with experimental uncertainties that are commonly associated with this analytical method.

For a number of compounds, melting points were determined in open capillary tubes either on a Mettler FP62 or on a Mettler FP81HT-FP90 apparatus. Melting points were measured with a temperature gradient of 3 or 10 ° C./min. Maximum temperature was 300° C. The melting point was read from a digital display.

For a number of compounds, melting points (m.p.) were determined with a WRS-2A melting point apparatus (Shanghai Precision and Scientific Instrument Co. Ltd.). Melting points were measured with a linear heating up rate of 0.2-5.0° C./minute. The reported values are melt ranges. The maximum temperature was 300° C. (indicated by WRS-2A).

TABLE 1

Analytical data. Retention time (R$_t$) in min., [M + H]$^+$ peak (protonated molecule), LCMS method and m.p. (melting point in ° C).

| Co. No. | Structure | m.p. | [M + H]$^+$ | R$_t$ | LCMS Method |
|---|---|---|---|---|---|
| 1 | 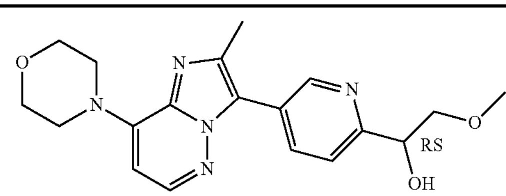 | 137.2 | 370 | 1.50 | 1 |
| 1a | 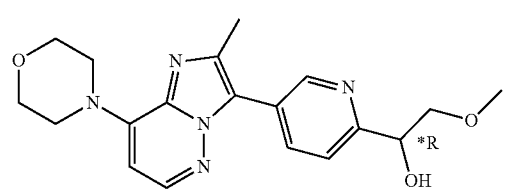 [SMILES: COCC(O)c1ccc(-c2c(C)nc3c(N4CCOCC4)ccnn23)cn1] | 134.9 | 370 | 1.50 | 1 |
| 1b | 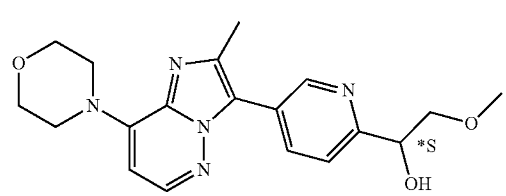 [SMILES: COCC(O)c1ccc(-c2c(C)nc3c(N4CCOCC4)ccnn23)cn1] | 135.7 | 370 | 1.50 | 1 |

TABLE 1-continued

Analytical data. Retention time (R$_t$) in min., [M + H]$^+$ peak (protonated molecule), LCMS method and m.p. (melting point in ° C).

| Co. No. | Structure | m.p. | [M + H]$^+$ | R$_t$ | LCMS Method |
|---|---|---|---|---|---|
| 2 | 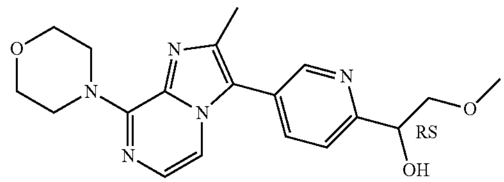 [SMILES: COCC(O)c1ccc(-c2c(C)nc3c(N4CCOCC4)nccn23)cn1] | 106.9 | 370 | 2.40 | 2 |
| 3 | 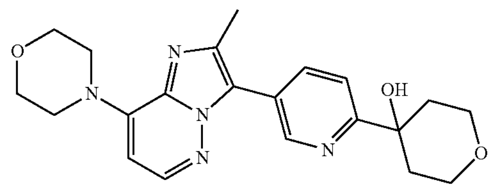 [SMILES: Cc1nc2c(N3CCOCC3)ccnn2c1-c1ccc(C2(O)CCOCC2)nc1] | 189.2 | 396 | 2.68 | 2 |
| 4 | 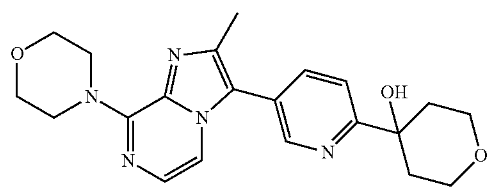 [SMILES: Cc1nc2c(N3CCOCC3)nccn2c1-c1ccc(C2(O)CCOCC2)nc1] | 181.6 | 396 | 2.60 | 2 |

SFC-MS Methods:

General Procedure

The SFC measurement was performed using an Analytical SFC system from Berger instrument comprises a FCM-1200 dual pump fluid control module for delivering carbon dioxide (CO$_2$) and modifier, a CTC Analytics automatic liquid sampler, a TCM-20000 thermal control module for column heating from room temperature to 80° C. An Agilent 1100 UV photodiode array detector equipped with a high-pressure flow cell standing up to 400 bars was used. Flow from the column was split to a MS spectrometer. The MS detector was configured with an atmospheric pressure ionization source. The following ionization parameters for the Waters ZQ mass spectrophotometer are: corona: 9 µa, source temp: 140° C., cone: 30 V, probe temp 450° C., extractor 3 V, desolvatation gas 400 L/hr, cone gas 70 L/hr. Nitrogen was used as the nebulizer gas. Data acquisition was performed with a Waters-Micromass MassLynx-Openlynx data system.

Method 1:

In addition to the general procedure: The chiral separation in SFC was carried out on a CHIRALCEL OD-H DAICEL column (5 µm, 4.6×250 mm) at 35° C. with a flow rate of 3.0 ml/min. The mobile phase is 70% CO$_2$, 30% iPrOH (+0.3% iPrNH$_2$) hold 7 min in isocratic mode.

TABLE 2

Analytical SFC data - R$_t$ means retention time (in minutes), [M + H]$^+$ means the protonated mass of the compound, method refers to the method used for SFC/MS analysis of enantiomerically pure compounds.

| Co. Nr. | R$_t$ | [M + H]$^+$ | UV Area % | Method | Isomer Elution Order* |
|---|---|---|---|---|---|
| 1a | 5.4 | 370 | 100 | 1 | A |
| 1b | 6.1 | 370 | 99.4 | 1 | B |

*A means the first isomer that elutes. B means the second isomer that elutes.

Optical Rotations:

Optical rotations were measured on a Perkin-Elmer 341 polarimeter with a sodium lamp and reported as follows: [α]° (λ, c g/100 ml, solvent, T° C.). $[α]_λ^T = (100α)/(l×c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

TABLE 3

Analytical data - Optical rotation values for enantiomerically pure compounds.

| Co. Nr. | [α] (°) | Wavelength (nm) | Concentration w/v % | Solvent | Temp. (° C.) |
|---|---|---|---|---|---|
| 1a | −44.7 | 589 | 0.5 | DMF | 20 |
| 1b | +40.8 | 589 | 0.5 | DMF | 20 |

Nuclear Magnetic Resonance (NMR)

For a number of compounds, $^1$HNMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard.

Compound 1

$^1$HNMR (400 MHz, CDCl$_3$) δ ppm 2.55 (s, 3 H), 3.45 (s, 3 H), 3.67 (dd, J=9.7, 6.7 Hz, 1 H), 3.75 (dd, J=9.9, 4.4 Hz, 1 H), 3.89-4.02 (m, 8 H), 4.06 (d, J=4.9 Hz, 1 H), 4.98 (dt, J=6.7, 4.6 Hz, 1 H), 6.11 (d, J=5.5 Hz, 1 H), 7.57 (d, J=8.3 Hz, 1 H), 7.99 (d, J=5.5 Hz, 1 H), 8.08 (dd, J=8.1, 2.3 Hz, 1 H), 8.83 (d, J=2.1, 0.7 Hz, 1 H).

Compound 1a $^1$HNMR (500 MHz, CDCl$_3$) δ ppm 2.54 (s, 3 H), 3.45 (s, 3 H), 3.67 (dd, J=9.8, 6.9 Hz, 1 H), 3.75 (dd, J=9.8, 4.3 Hz, 1 H), 3.87-4.00 (m, 8 H), 4.04 (br. s., 1 H), 4.98 (dd, J=6.1, 4.6 Hz, 1 H), 6.11 (d, J=5.8 Hz, 1 H), 7.57 (d, J=8.1 Hz, 1 H), 7.99 (d, J=5.5 Hz, 1 H), 8.08 (dd, J=8.1, 2.0 Hz, 1 H), 8.83 (d, J=1.4 Hz, 1 H).

Compound 1b $^1$HNMR (500 MHz, CDCl$_3$) δ ppm 2.55 (s, 3 H), 3.45 (s, 3 H), 3.67 (dd, J=9.5, 6.6 Hz, 1 H), 3.75 (dd, J=9.8, 4.3 Hz, 1 H), 3.88-4.00 (m, 8H), 4.03 (br. s., 1 H), 4.98 (dd, J=6.5, 4.5 Hz, 1 H), 6.11 (d, J=5.5 Hz, 1 H), 7.57 (d, J=8.1 Hz, 1 H), 7.99 (d, J=5.5 Hz, 1 H), 8.08 (dd, J=8.1, 2.0 Hz, 1 H), 8.83 (d, J=1.7 Hz, 1 H).

Compound 2

$^1$HNMR (400 MHz, CDCl$_3$) δ ppm 1.71 (br. s., 1 H), 2.45 (s, 3 H), 3.47 (s, 3 H), 3.71 (dd, J=9.7, 6.5 Hz, 1 H), 3.79 (dd, J=9.7, 4.2 Hz, 1 H), 3.90 (t, J=4.9 Hz, 4 H), 4.28 (t, J=4.6 Hz, 4 H), 5.01 (dd, J=6.5, 4.6 Hz, 1 H), 7.36 (d, J=4.6 Hz, 1 H), 7.39 (d, J=4.9 Hz, 1 H), 7.64 (d, J=7.9 Hz, 1 H), 7.80 (dd, J=8.1, 2.3 Hz, 1 H), 8.65 (d, J=1.6 Hz, 1 H).

Compound 3

$^1$HNMR (500 MHz, DMSO-d$_6$) δ ppm 1.54 (d, J=12.4 Hz, 2 H), 2.25 (td, J=12.6, 5.2 Hz, 2 H), 2.46 (s, 3 H), 3.72-3.87 (m, 8 H), 3.91-4.06 (m, 4 H), 5.34 (s, 1 H), 6.37 (d, J=5.5 Hz, 1 H), 7.82 (d, J=8.1 Hz, 1 H), 8.05-8.15 (m, 2 H), 8.81 (d, J=1.7 Hz, 1 H).

Compound 4

$^1$HNMR (400 MHz, CDCl$_3$) δ ppm 1.65 (br. d, J=12.0 Hz, 2 H), 2.21 (td, J=12.6, 5.5 Hz, 2 H), 2.46 (s, 3 H), 3.90 (dd, J=5.1, 4.6 Hz, 4 H), 3.94-4.09 (m, 4 H), 4.28 (t, J=4.6 Hz, 4 H), 4.99 (s, 1 H), 7.36 (d, J=4.4 Hz, 1 H), 7.39 (d, J=4.6 Hz, 1 H), 7.57 (dd, J=8.2, 0.8 Hz, 1 H), 7.83 (dd, J=8.2, 2.2 Hz, 1 H), 8.64 (dd, J=2.1, 0.9 Hz, 1 H).

Pharmacological Examples

The compounds provided in the present invention are inhibitors of PDE10, particularly, of PDE10A. The behaviour of the PDE10 inhibitors according to Formula (I) in vitro and using an apomorphine induced stereotypy model in vivo is shown in Table 4.

A) In Vitro Assay PDE10A

Human or rat recombinant PDE10A (hPDE10A2 or rPDE10A2) was expressed in Sf9 cells using a recombinant hPDE10A or rPDE10A baculovirus construct. Cells were harvested after 48 h of infection and the hPDE10A or rPDE10A protein was purified by metal chelate chromatography on Ni-sepharose 6FF. Tested compounds were dissolved and diluted in 100% DMSO to a concentration 100 fold of the final concentration in the assay. Compound dilutions (0.4 μl) were added in 384 well plates to 20 μl of incubation buffer (50 mM Tris pH 7.8, 8.3 mM MgCl$_2$, 1.7 mM EGTA). 10 μl of hPDE10A or rPDE10A enzyme in incubation buffer was added and the reaction was started by addition of 10 μl substrate to a final concentration of 60 nM cAMP and 0.008 μCi $^3$H-cAMP. The reaction was incubated for 60 min. at RT. After incubation, the reaction was stopped with 20 μl of stop solution consisting of 17.8 mg/ml PDE SPA (scintillation proximity assay) beads. After sedimentation of the beads during 30 min. the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve was fitted by a minimum sum of squares method to the plot of % of control value substracted with blanc value versus compound concentration and the half maximal inhibitory concentration (IC$_{50}$) value was derived from this curve. An overview of the results is shown in table 4 below.

B) Apomorphine-Induced Stereotypy in Rats (APO)

Apomorphine (1.0 mg/kg, i.v.)-induced stereotypy (compulsive sniffing, licking, chewing) was scored every 5 min. over the first hour after injection of apomorphine, following a 1 hour interval pre-treatment with the test compound. The score system was: (3) pronounced, (2) moderate, (1) slight, and (0) absent. Criteria for drug-induced inhibition of stereotypy: fewer than 6 scores of 3 (0.16% false positives), fewer than 6 scores of ≥2 (0.0% false positives), or fewer than 7 scores of ≥1 (0.81% false positives). The results of this test are shown in table 4 below.

TABLE 4

Pharmacological data for the compounds of the invention in vitro and in the inhibition of apomorphine-induced stereotypy in rats (APO). pIC$_{50}$ corresponds to the -log IC$_{50}$ expressed in mol/L. ED$_{50}$ is the dose (mg/kg body weight) at which 50% of the tested animals show the effect.

| Co. No. | PDE10A2 pIC$_{50}$ - human enzyme | PDE10A2 pIC$_{50}$ - rat enzyme | APO ED$_{50}$ (mg/kg) |
|---|---|---|---|
| 1 | 7.19 | 7.26 | 1.0* |
| 1a | 7.12 | 7.32 | 1.2 |
| 1b | 7.22 | 7.3 | 1.2 |
| 2 | 6.58 | n.t. | 0.31 |
| 3 | 7.56 | n.t. | 0.31 |
| 4 | 6.95 | n.t. | 0.31 |
| Co. No. 1 of WO2011/051342[a] | 7.22 | 7.24 | 1.3 |
| Co. No. 27 of WO2011/051342[a] | n.t. | 7.5 | n.d.‡ |
| Co. No. 16 of WO2011/110545[a] | 6.98 | 6.72 | 1.0 |
| Co. No. 25 of WO2011/110545[a] | 6.78 | 6.83 | 1.0 | n.t. means not tested; *means the compound was dosed orally; ‡ED$_{50}$ was not determined (compound was tested up to 2.5 mg/kg); [a]updated values are provided when the compound was further tested.

C) Plasma Protein Binding of Compounds 1a and 1b According to the Invention

Test System

The plasma protein binding and blood distribution was investigated in healthy human subjects. Fresh blood was collected and centrifugated (approximately 1700 g for 10 min, room temperature, Hettich Rotixa AP centrifuge). The experiment was started within 4 hours after blood collection.

Spike Solutions and Final Concentrations

The following spike solutions were used:

TABLE 5

Spike solutions and final concentrations.

| Spike solution | Final concentration |
|---|---|
| 10 and 1300 µg/mL | 0.1 and 13 µg/ml |

Plasma Protein Binding Experiment

Individual blank plasma samples from three healthy male subjects, tested in duplicate, were fortified with compound 1a or compound 1b at different concentrations (see Table 5). Plasma samples were spiked with 10 µl spike solution per ml of sample (1% ethanol (v/v)).

Fortified plasma was subjected to equilibrium dialysis (ED), for 4 h against a 0.067 M phosphate buffer, pH 7.17 at 37° C. in a Dianorm system with identical macro-1 Teflon cells and Spectra/Por® RC 2 dialysis membranes (MW cut-off 12-14 kDa). After dialysis, the contents of the two compartments of the dialysis cells were collected separately. The buffer samples were diluted with 1 mL of 5% Bovine Serum Albumin in a Phosphate buffer 0.05M, pH 7.5.

The plasma samples (before and after equilibrium dialysis) and buffer samples were analysed for compound 1a or compound 1b using a qualified chiral LC-MS/MS assay on a API4000 mass spectrometer (Applied Biosystems).

TABLE 6

Binding of compounds 1a and 1b at 0.1 and 13 µg/ml of compounds 1a or 1b to plasma proteins from human.

| | Free fraction | | | |
|---|---|---|---|---|
| | Compound 1a | | Compound 1b | |
| Human | 0.1 µg/ml | 13 µg/ml | 0.1 µg/ml | 13 µg/ml |
| Subject 1 | 47.3 | 43.9 | 54.9 | 51.9 |
| Subject 1* | 48.9 | 45.6 | 53.1 | 53.3 |
| Average | 48.1 | 44.8 | 54.0 | 52.6 |
| Subject 2 | 46.8 | 44.6 | 55.2 | 52.7 |
| Subject 2* | 50.1 | 46.1 | 57.4 | 46.6 |
| Average | 48.5 | 45.4 | 56.3 | 49.6 |
| Subject 3 | 47.6 | 46.5 | 46.9 | 51.4 |
| Subject 3* | 48.9 | 46.0 | 53.1 | 49.7 |
| Average | 48.3 | 46.2 | 50.0 | 50.5 |
| Average (S.D.) (n = 12) | 46.9 (1.8) | | 52.2 (3.2) | |

*means duplicate

No relevant concentration dependency in the plasma protein binding of compound 1a and compound 1b was detected within the concentration range tested (0.1 to 13 µg/ml). The percentage of free compound in plasma was on average (Table 7):

TABLE 7

Average percentage of free compound in plasma.

| Compound 1a | | Compound 1b | | Compound 1 of WO2011/051342 (males)[‡] | | | |
|---|---|---|---|---|---|---|---|
| 0.1 µg/ml | 13 µg/ml | 0.1 µg/ml | 13 µg/ml | 0.1 µg/ml | 1 µg/ml | 2 µg/ml | 5 µg/ml |
| 48.3 | 45.5 | 53.4 | 50.9 | 17.6 | 18.2 | 17.9 | 18.4 |

[‡]No relevant concentration dependency in the plasma protein binding of compound 1 of WO2011/051342 was detected within the concentration range tested.

Data Analysis

The fraction of the unbound test compound ($f_u$) was calculated as the ratio of the unbound concentration ($C_u$) in the buffer compartment to the total concentration ($C_{ED}$) in the protein compartment of the dialysis cells. The percentage of the free test compound was calculated as $f_u \times 100$.

$$f_u = \frac{C_u}{C_{ED}}$$

Results and Discussion

Binding of compound 1a and compound 1b at 0.1 and 13 µg/ml to plasma proteins was studied by means of equilibrium dialysis (Table 6).

D) Pharmacokinetics of Oral Microdose of Compound 1 According to the Invention and Compound 1 of WO2011/051342

Methods

The pharmacokinetics of an oral microdose of compound 1 according to the invention and compound 1 of WO2011/051342 was studied by a single-dose, open-label, parallel-group, randomized pharmacokinetic (PK) study. Each treatment group consisted of 6 subjects (healthy men between 18 to 55 years with a body mass index (BMI) between 18 and 30 kg/m² (inclusive) and body weight not less than 50 kg). Subjects were randomized to receive either compound 1 of WO2011/051342 or compound 1 (according to the invention) treatment.

Compound 1 of WO2011/051342 and compound 1 according to the invention were supplied as a 0.1 mg/mL oral solution containing HP-β-CD and citric acid in purified water. The pH of the solution was adjusted to pH 2.0 by the use of hydrochloric acid. Subjects were admitted to the investigational site on Day -1. Following an overnight fast of at least 10 hours, subjects received a single oral aqueous solution of 100 µg/mL of compound 1 of WO2011/051342 or compound 1 according to the invention, with 240 mL of noncarbonated water as per randomization in the morning of Day 1 between 7:00 AM and 10:30 AM. Drinks were not allowed from 1 hour prior until 1 hour after drug administration. Blood samples were collected at specified time points to measure compound 1 of WO2011/051342 or compound 1 (according to the invention) plasma concentrations. Subjects were discharged on Day 3 after collecting the 48-hour PK sample. Subjects returned to the clinical unit on the morning of Day 4 for the 72-hour PK blood sampling.

A pharmacogenomic blood sample (9 mL) was collected from all enrolled subjects on Day 1, for which subjects had given consent separately.

All subjects returned to the clinical unit for a follow-up visit (within 7 days postdose or early withdrawals).

The total study duration for each subject was approximately 4 weeks (including a 21-day Screening phase and a 7-day Open-label treatment phase which included a follow-up visit).

Pharmacokinetic Evaluation

Venous blood samples of 6 mL for the measurement of compound 1 of WO2011/051342 or compound 1 according to the invention plasma concentrations were collected at specified time points.

Plasma samples were analyzed to determine concentrations of compound 1 of WO2011/051342 or compound 1 according to the invention using a qualified liquid chromatography/mass spectrometry/mass spectrometry (LC-MS/MS) method.

Sample Size Determination

For this exploratory study the sample size was not based on formal statistical calculations. The number of subjects per treatment was the customary sample size employed in early development studies, and it was expected to allow assessment of the PK profile. Based on previous studies, the point estimate of the terminal half-life was anticipated to fall within 71% and 140% of the true value with 90% of confidence.

Pharmacokinetic Analysis

Pharmacokinetic analyses were performed for all subjects' data who received a dose of compound 1 of WO2011/051342 and compound 1 according to the invention. Plasma concentrations versus time profiles were plotted for each subject. Mean concentration versus time profiles were plotted for each compound, based on planned blood sampling times. Descriptive statistics, including arithmetic mean, standard deviation, CV, geometric mean, median, minimum, and maximum were calculated for the plasma concentrations at each sampling time and for all PK parameters of compound 1 of WO2011/051342 and compound 1 according to the invention.

Pharmacokinetic Results

A biphasic concentration-time curve was observed. Absorption was fast with individual $t_{max}$ ranging from 0.5 to 1 hour.

TABLE 8

Plasma PK parameters of compound 1 of WO2011/051342 and compound 1 according to the invention, after a single oral dose of 100 µg in healthy subjects under fasted conditions.

| | A single oral dose of 100 µg compound 1 of WO2011/051342 | | | A single oral dose of 100 µg compound 1 according to the invention | | |
|---|---|---|---|---|---|---|
| | N | Mean | SD | N | Mean | SD |
| $C_{max}$, pg/mL | 6 | 367 | 157 | 6 | 758 | 208 |
| $t_{max}$, h[a] | 6 | 0.50 (0.50-0.75) | | 6 | 0.64 (0.50-0.98) | |
| $AUC_{last}$, pg·h/mL | 6 | 595 | 311 | 6 | 2609 | 1347 |
| $AUC_\infty$, pg·h/mL | 5 | 665 | 313 | 6 | 2637 | 1355 |
| $\lambda_z$, 1/h | 5 | 0.158 | 0.0824 | 6 | 0.148 | 0.0722 |
| $t_{1/2}$, h | 5 | 5.4 | 2.6 | 6 | 5.7 | 2.5 |
| $V_d/F$, L | 5 | 1181 | 174 | 6 | 333 | 117 |
| CL/F, L/h | 5 | 183 | 90.8 | 6 | 47.9 | 24.6 |

[a]Median (Min-Max) reported for $t_{max}$
[b]Individual values reported for n = 2
In the table, $C_{max}$ is the peak plasma concentration of the compound after administration, $t_{max}$ is the time to reach $C_{max}$, AUC is the area under the curve of the concentration-time curve, $\lambda_z$ is the terminal elimination rate constant, $t_{1/2}$ represents the elimination half-life, $V_d$ represents volume of distribution, F represents bioavailability, CL is the volume of plasma cleared of the compound per unit time.

$V_d/F$ was approximately 3.5-fold lower for compound 1 according to the invention (333±117 L) compared to compound 1 of WO2011/051342 (1181±174 L) and Cl/F was approximately 3.8-fold lower for compound 1 according to the invention (47.9±24.6 L/h) compared to compound 1 of WO2011/051342 (183±90.8 L/h).

Prophetic Composition Examples

"Active ingredient" as used throughout these examples relates to a final compound of Formula (I), the pharmaceutically acceptable salts thereof, the solvates and the stereochemically isomeric forms thereof.

Typical examples of recipes for the Formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

| | |
|---|---|
| Active ingredient | 5 to 1000 mg |
| Stearyl alcohol | 3 g |
| Lanoline | 5 g |

The invention claimed is:

1. A compound of Formula (I)

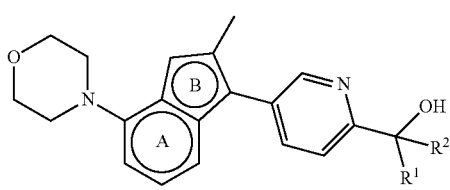

(I)

or a stereoisomeric form thereof, wherein
R¹ is H and R² is

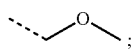

or wherein R¹ and R², taken together with the carbon atom to which they are attached, form a radical of Formula

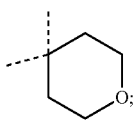

and
the bicycle

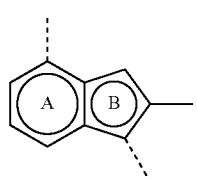

is a bicycle of Formula a)

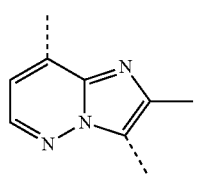

or a bicycle of Formula b)

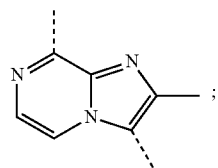

or a pharmaceutically acceptable salt or a solvate thereof.

2. The compound according to claim 1, having the Formula (I')

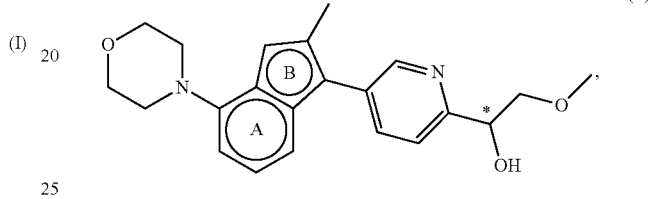

(I')

or a stereoisomeric form, or a salt or a solvate thereof.

3. The compound according to claim 1, having the Formula (I")

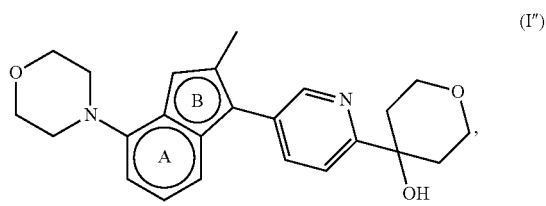

(I")

or a stereoisomeric form, or a salt or a solvate thereof.

4. The compound according to claim 1, selected from the group consisting of

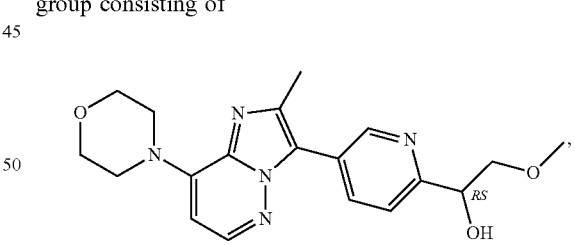

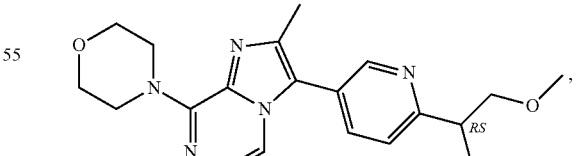

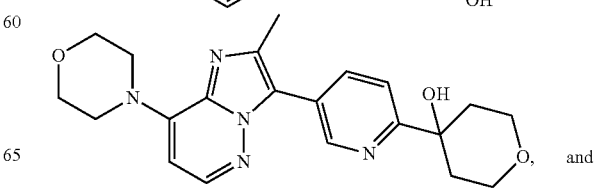

and

-continued

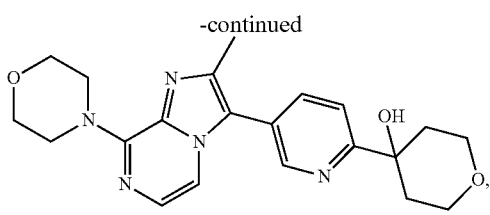

or a stereoisomeric form thereof, or a pharmaceutically acceptable salt or a solvate thereof.

5. The compound according to claim 1, selected from

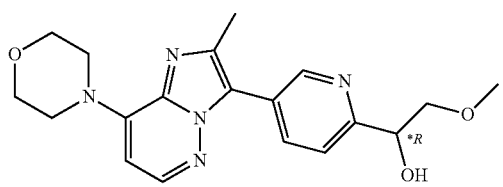 [SMILES: COCC(O)c1ccc(-c2c(C)nc3c(N4CCOCC4)ccnn23)cn1]

having an optical rotation [α]=−44.7° (589 nm, c 0.5 g/100 mL, DMF, 20° C.); or

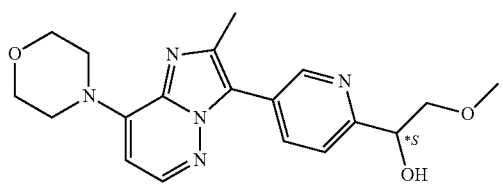 [SMILES: COCC(O)c1ccc(-c2c(C)nc3c(N4CCOCC4)ccnn23)cn1]

having an optical rotation [α]=+40.8° (589 nm, c 0.5 g/100 mL, DMF, 20° C.);

or a pharmaceutically acceptable salt or a solvate thereof.

6. A pharmaceutical composition comprising a therapeutically effective amount of a compound according to claim 1 and a pharmaceutically acceptable carrier or excipient.

7. A method for the treatment of a central nervous system disorder in which the PDE10 enzyme is involved in a subject with a central nervous system disorder, wherein the central nervous system disorder is selected from the group of psychotic disorders and conditions, anxiety disorders, movement disorders, drug abuse, mood disorders, neurodegenerative disorders, cognitive disorders, pain, autistic disorders; and of metabolic disorders comprising administering a therapeutically effective amount of a compound of claim 1 to said subject in need of treatment for said central nervous system disorder.

8. The method according to claim 7, wherein
the psychotic disorders and conditions are selected from the group of schizophrenia, schizophreniform disorder, schizoaffective disorder, delusional disorder, substance-induced psychotic disorder, personality disorders of the paranoid type, and personality disorder of the schizoid type;
the anxiety disorders are selected from the group of panic disorder, agoraphobia, specific phobia, social phobia, obsessive-compulsive disorder, post-traumatic stress disorder, acute stress disorder, and generalized anxiety disorder;
the movement disorders are selected from the group of Huntington's disease, dyskinesia, Parkinson's disease, restless leg syndrome, essential tremor, Tourette's syndrome and other tic disorders;
the drug abuse is selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence, and opioid withdrawal;
the mood disorders are selected from the group of depression, mania, bipolar disorder I, bipolar disorder II, cyclothymic disorder, dysthymic disorder, major depressive disorder, treatment-resistant depression, and substance-induced mood disorder;
the neurodegenerative disorders are selected from the group of Parkinson's disease, Huntington's disease, Alzheimer's disease, multi-infarct dementia, AIDS-related dementia or frontotemporal dementia;
the cognitive disorders are selected from the group of delirium, substance-induced persisting delirium, dementia, dementia of the Alzheimer's type, vascular dementia, dementia due to HIV disease, dementia due to intracranial tumours, cerebral trauma or head trauma, dementia due to stroke, dementia due to Parkinson's disease, dementia due to Huntington's disease, dementia due to Pick's disease, dementia due to Creutzfeldt-Jakob Disease, dementia due to Lewy body disease, substance-induced persisting dementia, dementia due to multiple etiologies, dementia not otherwise specified, mild cognitive impairment, age-related cognitive impairment, senility, amnestic disorder, post-traumatic stress disorder, mental retardation, learning disorder, attention-deficit/hyperactivity disorder (ADHD), and Down's syndrome;
pain includes acute and chronic states, severe pain, intractable pain, neuropathic pain and post-traumatic pain;
the metabolic disorders are selected from the group of diabetes type 1, type 2 diabetes, syndrome X, impaired glucose tolerance, impaired fasting glucose, gestational diabetes, maturity-onset diabetes of the young (MODY), latent autoimmune diabetes adult (LADA), associated diabetic dyslipidemia, hyperglycemia, hyperinsulinemia, dyslipidemia, hypertriglyceridemia, and insulin resistance.

9. A process for preparing a pharmaceutical composition comprising mixing a pharmaceutically acceptable carrier with a therapeutically effective amount of a compound as defined in claim 1.

10. A pharmaceutical composition comprising
(a) a compound as defined in claim 1; and
(b) an additional pharmaceutical agent.

11. A process for the preparation of a compound according to claim 1, wherein $R^1$ and $R^2$ are as defined in claim 1, comprising the step of

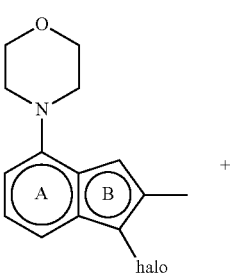

(II)

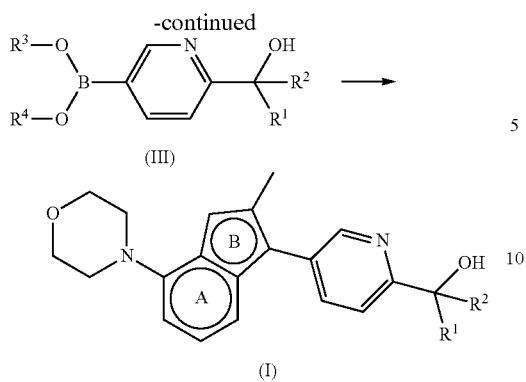

reacting a compound of Formula (II) wherein halo represents bromo or iodo with a boronic acid or a compound of Formula (III), wherein $R^3$ and $R^4$ may each be independently selected from hydrogen or $C_{1-4}$alkyl, or may be taken together to form a bivalent radical of Formula —CH$_2$—CH$_2$—, —CH$_2$—CH$_2$—CH$_2$—, or —C(CH$_3$)$_2$C(CH$_3$)$_2$—, in the presence of a suitable catalyst and a suitable base, in a suitable inert solvent, under heating.

12. A method for the treatment of a central nervous system disorder in which the PDE10 enzyme is involved in a subject with a central nervous system disorder, wherein the central nervous system disorder is selected from the group of psychotic disorders and conditions, anxiety disorders, movement disorders, drug abuse, mood disorders, neurodegenerative disorders, cognitive disorders, pain, autistic disorders; or a metabolic disorder, comprising administering to a subject in need thereof, a therapeutically effective amount of a compound according to claim 4.

13. The method according to claim 12, wherein
the psychotic disorders and conditions are selected from the group of schizophrenia, schizophreniform disorder, schizoaffective disorder, delusional disorder, substance-induced psychotic disorder, personality disorders of the paranoid type, and personality disorder of the schizoid type;
the anxiety disorders are selected from the group of panic disorder, agoraphobia, specific phobia, social phobia, obsessive-compulsive disorder, post-traumatic stress disorder, acute stress disorder, and generalized anxiety disorder;
the movement disorders are selected from the group of Huntington's disease, dyskinesia, Parkinson's disease, restless leg syndrome, essential tremor, Tourette's syndrome and other tic disorders;
the drug abuse is selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence, and opioid withdrawal;
the mood disorders are selected from the group of depression, mania, bipolar disorder I, bipolar disorder II, cyclothymic disorder, dysthymic disorder, major depressive disorder, treatment-resistant depression, and substance-induced mood disorder;
the neurodegenerative disorders are selected from the group of Parkinson's disease, Huntington's disease, Alzheimer's disease, multi-infarct dementia, AIDS-related dementia or frontotemperal dementia;
the cognitive disorders are selected from the group of delirium, substance-induced persisting delirium, dementia, dementia of the Alzheimer's type, vascular dementia, dementia due to HIV disease, dementia due to intracranial tumours, cerebral trauma or head trauma, dementia due to stroke, dementia due to Parkinson's disease, dementia due to Huntington's disease, dementia due to Pick's disease, dementia due to Creutzfeldt-Jakob Disease, dementia due to Lewy body disease, substance-induced persisting dementia, dementia due to multiple etiologies, dementia not otherwise specified, mild cognitive impairment, age-related cognitive impairment, senility, amnestic disorder, post-traumatic stress disorder, mental retardation, learning disorder, attention-deficit/hyperactivity disorder (ADHD), and Down's syndrome;
pain includes acute and chronic states, severe pain, intractable pain, neuropathic pain and post-traumatic pain;
the metabolic disorders are selected from the group of diabetes type 1, type 2 diabetes, syndrome X, impaired glucose tolerance, impaired fasting glucose, gestational diabetes, maturity-onset diabetes of the young (MODY), latent autoimmune diabetes adult (LADA), associated diabetic dyslipidemia, hyperglycemia, hyperinsulinemia, dyslipidemia, hypertriglyceridemia, and insulin resistance.

* * * * *